US009814471B2

(12) United States Patent
Goldberg et al.

(10) Patent No.: US 9,814,471 B2
(45) Date of Patent: Nov. 14, 2017

(54) GLENOID ARTHROPLASTY AND OFFSET REAMERS

(71) Applicant: CATALYST ORTHOSCIENCE INC., Naples, FL (US)

(72) Inventors: Steven S. Goldberg, Naples, FL (US); Daniel F. Justin, Orlando, FL (US); Daniel J. Triplett, Providence, UT (US)

(73) Assignee: CATALYST ORTHOSCIENCE INC., Naples, FL (US)

( * ) Notice: Subject to any disclaimer, the term of this patent is extended or adjusted under 35 U.S.C. 154(b) by 0 days.

(21) Appl. No.: 14/592,837

(22) Filed: Jan. 8, 2015

(65) Prior Publication Data

US 2015/0119891 A1    Apr. 30, 2015

Related U.S. Application Data

(63) Continuation-in-part of application No. 14/042,258, filed on Sep. 30, 2013.

(Continued)

(51) Int. Cl.
*A61B 17/00* (2006.01)
*A61B 17/16* (2006.01)
(Continued)

(52) U.S. Cl.
CPC ...... *A61B 17/1684* (2013.01); *A61B 17/1631* (2013.01); *A61B 17/1778* (2016.11); *A61F 2/4081* (2013.01)

(58) Field of Classification Search
CPC ... A61B 17/1684; A61B 17/175; A61B 17/15; A61B 17/1666; A61B 17/17; A61B 2017/1778; A61B 17/00; A61B 17/1631; A61B 17/1637; A61B 2017/0046; A61B 2017/90; A61B 17/14; A61B 17/141; A61B 17/16; A61B 17/1622; A61B 17/1642; A61F 2002/30884; A61F 2/4014; A61F 2002/30299; A61F 2002/30538; A61F 2002/30892; A61F 2002/30904;
(Continued)

(56) References Cited

U.S. PATENT DOCUMENTS 4,106,130 A    8/1978  Scales
4,206,517 A    6/1980  Pappas et al.
(Continued)

FOREIGN PATENT DOCUMENTS

AU    2013209336    2/2014
CA    2821529    1/2014
(Continued)

*Primary Examiner* — Ann Schillinger
(74) *Attorney, Agent, or Firm* — Maywood IP Law; G. Jo Hays; David W. Meibos

(57) ABSTRACT

Arthroplasty components include an articular surface and a bone-facing surface. The bone-facing surface bears at least one anchoring element adapted for an oblique implantation trajectory. The articular surface includes a larger radius of curvature in the superior-inferior direction than in the anterior-posterior direction. An inferior chamfer may be present on the articular surface. Instruments and implantation methods are also disclosed. Reamers include reamer heads coupled to various offset shaft configurations.

17 Claims, 35 Drawing Sheets

Related U.S. Application Data

(60) Provisional application No. 61/925,893, filed on Jan. 10, 2014, provisional application No. 61/776,398, filed on Mar. 11, 2013.

(51) Int. Cl.
*A61B 17/17* (2006.01)
*A61F 2/40* (2006.01)

(58) Field of Classification Search
CPC ...... A61F 2002/4623; A61F 2002/4635; A61F 2/4081; A61F 2/46; A61F 2002/30242
See application file for complete search history.

(56) References Cited

U.S. PATENT DOCUMENTS

| | | | |
|---|---|---|---|
| 4,550,450 A | 11/1985 | Kinnett | |
| 4,865,605 A | 9/1989 | Dines | |
| 4,964,865 A | 10/1990 | Burkhead | |
| 4,986,833 A | 1/1991 | Worland | |
| 5,030,219 A | 7/1991 | Matsen, III | |
| 5,032,132 A | 7/1991 | Matsen, III | |
| 5,383,936 A | 1/1995 | Kubein Meesenburg | |
| 5,489,310 A | 2/1996 | Mikhail | |
| 5,702,447 A | 12/1997 | Walch | |
| 5,723,018 A | 3/1998 | Cyprien | |
| 5,769,856 A | 6/1998 | Dong | |
| 5,800,551 A | 9/1998 | Williamson | |
| 5,814,049 A | 9/1998 | Pratt | |
| 5,919,195 A * | 7/1999 | Wilson et al. | 606/80 |
| 5,928,285 A | 7/1999 | Bigliani | |
| 5,944,758 A | 8/1999 | Mansat | |
| 5,976,144 A | 11/1999 | Fishbein | |
| 6,129,732 A | 10/2000 | Lechot | |
| 6,245,074 B1 | 6/2001 | Allard | |
| 6,364,910 B1 | 4/2002 | Schultz | |
| 6,379,386 B1 | 4/2002 | Resch | |
| 6,406,495 B1 | 6/2002 | Schoch | |
| 6,475,221 B1 | 11/2002 | White | |
| 6,673,115 B2 | 1/2004 | Resch | |
| 6,679,916 B1 | 1/2004 | Frankle | |
| 6,783,549 B1 | 8/2004 | Stone et al. | |
| 6,875,234 B2 | 4/2005 | Lipman | |
| 6,911,047 B2 | 6/2005 | Rockwood | |
| 7,008,430 B2 | 3/2006 | Dong | |
| 7,048,740 B2 | 5/2006 | White | |
| 7,160,328 B2 | 1/2007 | Rockwood | |
| 7,204,854 B2 | 4/2007 | Guederian | |
| 7,217,272 B2 | 5/2007 | Salyer | |
| 7,294,149 B2 | 11/2007 | Hozack | |
| 7,329,284 B2 | 2/2008 | Maroney | |
| 7,588,572 B2 | 9/2009 | White | |
| 7,621,962 B2 | 11/2009 | Lakin | |
| 7,670,382 B2 | 3/2010 | Parrott | |
| 7,780,669 B2 | 8/2010 | Lechot | |
| 7,815,685 B2 | 10/2010 | Farrar | |
| 7,867,234 B2 | 1/2011 | Collazo | |
| 8,007,538 B2 | 8/2011 | Gunther | |
| 8,038,719 B2 | 10/2011 | Gunther | |
| 8,048,161 B2 | 11/2011 | Guederian | |
| 8,080,063 B2 | 12/2011 | Ferrand | |
| 8,157,866 B2 | 4/2012 | Winslow | |
| 8,308,809 B2 | 11/2012 | Bishop | |
| 8,425,614 B2 | 4/2013 | Winslow | |
| 8,444,646 B2 | 5/2013 | Long | |
| 8,465,548 B2 | 6/2013 | Long | |
| 8,475,460 B1 * | 7/2013 | Roger | A61B 17/1666 606/80 |
| 8,480,674 B1 | 7/2013 | Roger | |
| 8,540,778 B2 | 9/2013 | Rhodes | |
| 8,591,592 B2 | 11/2013 | Dreyfuss | |
| 8,673,015 B2 | 3/2014 | Maroney | |
| 8,764,836 B2 | 7/2014 | De Wilde | |
| 8,778,028 B2 | 7/2014 | Gunther | |
| 8,870,962 B2 | 10/2014 | Roche | |
| 8,876,907 B2 | 11/2014 | Baptista | |
| 8,974,537 B2 | 3/2015 | Dreyfuss | |
| D730,522 S | 5/2015 | Goldberg | |
| 9,119,643 B2 | 9/2015 | Winslow | |
| 9,180,016 B2 | 11/2015 | Maroney | |
| 9,233,003 B2 | 1/2016 | Roche | |
| 9,237,894 B2 | 1/2016 | Hernandez | |
| 9,283,076 B2 | 3/2016 | Sikora | |
| 9,351,844 B2 | 5/2016 | Walch | |
| D759,819 S | 6/2016 | Goldberg | |
| 9,370,428 B2 | 6/2016 | Winslow | |
| 9,433,507 B2 | 9/2016 | Reubelt | |
| 9,474,619 B2 | 10/2016 | Reubelt | |
| 9,610,166 B2 | 4/2017 | Gunther | |
| 2002/0082702 A1 | 6/2002 | Resch | |
| 2003/0187449 A1* | 10/2003 | McCleary et al. | 606/80 |
| 2003/0204263 A1 | 10/2003 | Justin et al. | |
| 2005/0049709 A1 | 3/2005 | Tornier | |
| 2005/0222572 A1* | 10/2005 | Chana | 606/81 |
| 2006/0074430 A1 | 4/2006 | Deffenbaugh | |
| 2006/0094958 A1* | 5/2006 | Marquart | A61B 17/1662 600/434 |
| 2006/0111787 A1 | 5/2006 | Bailie et al. | |
| 2007/0055380 A1 | 3/2007 | Berelsman | |
| 2007/0142917 A1 | 6/2007 | Roche | |
| 2007/0219637 A1 | 9/2007 | Berelsman | |
| 2007/0219638 A1 | 9/2007 | Jones | |
| 2007/0225817 A1 | 9/2007 | Reubelt | |
| 2007/0225818 A1 | 9/2007 | Reubelt | |
| 2008/0109000 A1 | 5/2008 | Maroney | |
| 2008/0147070 A1 | 6/2008 | Michel | |
| 2009/0125113 A1 | 5/2009 | Guederian | |
| 2009/0192621 A1 | 7/2009 | Winslow et al. | |
| 2009/0226068 A1 | 9/2009 | Fitz | |
| 2010/0087876 A1 | 4/2010 | Gunther | |
| 2010/0087877 A1 | 4/2010 | Gunther | |
| 2010/0161065 A1 | 6/2010 | Williams | |
| 2010/0241235 A1 | 9/2010 | Basamania | |
| 2010/0268239 A1 | 10/2010 | Sikora | |
| 2011/0035013 A1 | 2/2011 | Winslow | |
| 2011/0106266 A1 | 5/2011 | Schwyzer | |
| 2011/0230972 A1 | 9/2011 | Katrana | |
| 2012/0130498 A1 | 5/2012 | Long | |
| 2012/0130500 A1 | 5/2012 | Maroney | |
| 2012/0209392 A1 | 8/2012 | Angibaud | |
| 2012/0310360 A1 | 12/2012 | Parrott | |
| 2013/0024000 A1 | 1/2013 | Bojarski | |
| 2013/0144393 A1 | 6/2013 | Mutchler | |
| 2013/0166033 A1 | 6/2013 | Gunther | |
| 2014/0031945 A1 | 1/2014 | Baptista | |
| 2014/0257495 A1 | 9/2014 | Goldberg | |
| 2015/0320567 A1 | 11/2015 | Terrill | |
| 2016/0089164 A1 | 3/2016 | Winslow | |
| 2016/0095607 A1 | 4/2016 | Hernandez | |
| 2016/0242921 A1 | 8/2016 | Walch | |
| 2016/0287266 A1 | 10/2016 | Sikora | |
| 2017/0014238 A1 | 1/2017 | Reubelt | |
| 2017/0042689 A1 | 2/2017 | Goldberg | |

FOREIGN PATENT DOCUMENTS

| | | |
|---|---|---|
| CN | 101442961 | 11/2012 |
| CN | 102014800 | 4/2014 |
| CN | 105377195 | 3/2016 |
| DE | 10130796 | 1/2003 |
| DE | 10134511 | 2/2003 |
| EP | 1518519 | 3/2005 |
| EP | 1159939 | 7/2005 |
| EP | 2238949 | 10/2010 |
| EP | 2446859 | 5/2012 |
| EP | 2559406 | 2/2013 |
| EP | 2689751 | 1/2014 |
| EP | 2967892 | 1/2016 |
| FR | 2825263 | 12/2002 |
| FR | 2836821 | 5/2004 |
| GB | 2308068 | 9/1999 |
| WO | WO9815241 | 4/1998 |
| WO | WO0018335 | 4/2000 |
| WO | WO0217822 | 3/2002 |

(56) References Cited

FOREIGN PATENT DOCUMENTS

| | | |
|---|---|---|
| WO | WO2006110896 | 10/2006 |
| WO | WO2007109800 | 9/2007 |
| WO | WO2009108591 | 9/2009 |
| WO | WO2012030794 | 3/2012 |
| WO | WO2013020026 | 2/2013 |
| WO | WO2014005644 | 1/2014 |
| WO | WO2014164265 | 10/2014 |
| WO | WO2015106136 | 7/2015 |

* cited by examiner

GLENOID ARTHROPLASTY AND OFFSET REAMERS

CROSS-REFERENCE TO RELATED APPLICATIONS

The present application claims the benefit of:

U.S. Provisional Patent Application Ser. No. 61/925,893, entitled OFFSET REAMERS, which was filed on Jan. 10, 2014.

The present application is also a continuation-in-part of:

U.S. patent application Ser. No. 14/042,258, entitled GLENOID ARTHROPLASTY, which was filed on Sep. 30, 2013.

U.S. patent application Ser. No. 14/042,258 claims the benefit of:

U.S. Provisional Patent Application Ser. No. 61/776,398, entitled OBLIQUE-INSERTION ANCHORING MECHANISM FOR GLENOID PROSTHETIC COMPONENT, which was filed on Mar. 11, 2013.

The foregoing are incorporated by reference as though set forth herein in their entirety.

BACKGROUND

The present disclosure relates to anchoring elements and articular surfaces for human or veterinary implants. The disclosed anchoring elements are useful in situations where exposure is difficult, the implantation trajectory is oblique to the implantation site, or the implantation site is tapered, conical, or wedge-shaped. For example, the disclosed anchoring elements are useful in the context of a glenoid implant for shoulder arthroplasty, so that the preparation of the glenoid and implantation of the glenoid component take place along an oblique surgical access and implantation trajectory. An oblique approach, or an antero-lateral approach, to the glenoid is technically simpler and less invasive than a lateral trajectory to the glenoid. This disclosure is made in the context of a glenoid component for shoulder arthroplasty for the purpose of illustrating the relevant principles of the technology.

In total shoulder arthroplasty, a glenoid implant is attached to a prepared glenoid or scapula, and a humeral implant is attached to a prepared humerus. The humeral implant usually includes a ball or convex articular surface at a proximal end thereof which engages and moves relative to a socket or concave articular surface formed in a lateral aspect of the glenoid implant, although this arrangement is sometimes reversed so that the humeral implant includes the convex articular surface and the glenoid implant includes the convex articular surface. The ligaments and muscles of the shoulder surround the implants and maintain the humeral implant against the glenoid implant, while at the same time allowing relative movement therebetween.

Current implants frequently have a central peg or keel, occasionally with two or three small peripheral supporting pegs. These implants rely on the centrally placed anchoring element to provide the majority of the fixation. In situations where the surgeon encounters bone defects, bone cysts, or where a prior component has been removed, there is often a central defect in the bone where fixation is not possible.

Current instruments for standard glenoid arthroplasty, including drill bits, reamers, and trial implant components, and final implant components are frequently designed for the surgeon to approach the scapula along a direction perpendicular to the face of the glenoid portion of the scapula; this may be referred to as a direct lateral trajectory. However, the standard incisions and safest surgical approach for glenoid arthroplasty provide exposure for the surgeon which is more oblique, or antero-lateral. In order to facilitate the insertion of instruments perpendicular to the face of the glenoid, the surgeon may find it necessary to resect the articular portion of the humeral head and forcefully retract the patient's skin, muscle and remaining humerus out of the way posteriorly to obtain adequate exposure. In doing so, the surgeon may potentially injure nerves or blood vessels. Often the surgeon will purposely cut the biceps tendon or portions of the pectoralis major tendon to improve exposure to facilitate this step, as well as releasing the glenohumeral ligaments. All of this dissection, retraction, and removal of bone and soft tissue is done in order to allow the surgeon enough room to implant the glenoid prosthetic component.

Thus, there is a need for an implant anchoring mechanism that can be inserted from an oblique angle to allow for a less invasive and technically simpler surgical operation, for example, for anchoring a glenoid prosthetic component to scapular bone.

The present disclosure sets forth an oblique-insertion anchoring mechanism for securing a glenoid prosthetic component to scapular bone. The anchoring mechanism can be inserted from an oblique angle to allow for a less invasive and technically simpler surgical operation. The anchoring mechanism is formed from a rounded dowel which projects from the medial aspect of a glenoid prosthetic component. The dowel projects at an angle which is not perpendicular to, or normal to, the medial side of the glenoid component, but is instead an acute angle less than 90 degrees. In the acute angle between the dowel and the medial side of the glenoid component there is a triangular reinforcement plate which buttresses the dowel and arises at a supplementary angle from the medial side of the glenoid component. The dowel and the edge of the reinforcement plate meet at the apex of the triangle.

It is contemplated that the number and location or placement of the anchoring elements will vary to accommodate different clinical situations.

The anchoring elements disclosed herein may be placed peripherally in a ring orientation, avoiding a bony central defect. Anchoring elements placed more peripherally provide more resistance to the effects of shear forces caused by the pressure of the humeral head during edge loading, as the distance and resultant lever arm decrease.

Biomechanically, the triangular arrangement of the dowel with the reinforcement plate allows the anchoring element to stabilize the body of the prosthesis from both legs of the triangular base to protect against both anterior and posterior eccentric forces. The triangular base of the anchoring element provides balanced anchoring to resist the anterior and posterior directed forces. The disclosed technology has fixation at both legs of the triangle, symmetric in distance from the edges of the body of the prosthesis, and all along the base of the triangle as well. The triangular shape also provides much larger surface area to resist superior and inferior directed forces than pegs alone. This is in contrast to a simple obliquely oriented peg which places the point of fixation of implant off center, allowing liftoff at the side farthest from the peg.

The disclosed design of the anchoring element may be even more preferable than traditional designs when glenoid deformity is present. Glenoid retroversion and glenoid vault bone loss are commonly seen in cases of advanced arthritis and the present design better fits the bony anatomy in these cases. This technology may also be preferable for revision glenoid arthroplasty operations.

The anchoring elements disclosed herein allow the prosthetic component to be inserted at an oblique angle. Therefore, there is less need to forcefully retract bone or soft tissues to obtain adequate exposure. The surgeon may be able to implant the prosthetic component without cutting the pectoralis major, the biceps tendon, or the glenohumeral ligaments. These tendons and ligaments serve as static and dynamic stabilizers of the humeral head during normal motion. If left intact, humeral motion remains more controlled and centered, reducing the incidence of humeral translation and contact with the far peripheral edges of the glenoid component. Reducing edge-loading results in less loosening forces transmitted to the anchoring elements, which is a common mode of failure of glenoid prosthetic components and total shoulder arthroplasty overall. Furthermore, the surgeon may not be compelled to resect the humeral head and may choose instead to use a bone-preserving humeral resurfacing arthroplasty component during the operation, which may further reduce operative time, blood loss and bone removal.

The inferior chamfer design of the lateral bearing surface of the glenoid component minimizes the incidence of impingement between the humeral component and the inferior articular margin of the glenoid prosthesis, thus reducing the likelihood of implant loosening and wear. Humeral impingement on the inferior glenoid is reported to be a cause of implant loosening and wear. Retrieval studies of loose failed glenoid implants have repeatedly demonstrated deformation at this inferior location.

For at least these reasons, the disclosed technology may simplify the operation, shorten the length of the operation, reduce soft-tissue dissection, reduce risk of neurovascular injury, reduce blood loss, reduce the need for bone resection, and may improve implant longevity.

Preservation of soft-tissues in glenoid preparation, optionally combined with the use of a humeral resurfacing component, may make shoulder arthroplasty more appealing for younger patients with significant degenerative disease, a patient group currently generally discouraged from undergoing shoulder arthroplasty.

An objective of the technology is to disclose a unique positioning of a dowel with planar buttress element in a glenoid prosthetic component.

Another objective of the technology is to disclose an improved glenoid prosthetic component that permit placement of anchoring elements in locations to better replicate normal human anatomy.

Yet another objective of the technology is to disclose an improved glenoid component that is inserted obliquely.

Yet another objective of the technology is to disclose an improved glenoid component having a dowel designed to match the specific anatomic shape of the surrounding bone.

Yet another objective of the technology is to disclose an improved glenoid prosthetic component having unique differential radius of curvature in the superior-inferior and anterior-posterior directions.

Yet another objective of the technology is to disclose an improved glenoid prosthetic component having a unique inferior chamfer.

Reamers are used in various medical procedures to prepare or shape bone surfaces. For example, reamers are used in various joint arthroplasty procedures. One example of an arthroplasty procedure is shoulder arthroplasty. Reamers may be used in shoulder arthroplasty procedures to prepare or shape bone surfaces on the glenoid or on the humeral head. Reamers may be used to prepare or shape bone surfaces which are planar, concave, convex, spherical, conical, or other surfaces of revolution.

In shoulder arthroplasty, the humeral head is in close proximity to the glenoid. The humeral head can interfere with an axial reamer (a conventional straight shaft instrument whose cutting face is perpendicular to the shaft axis) for preparation of the glenoid socket. Similar conditions exist in other joints of the body, such as the elbow, wrist, hip, knee, ankle, or joints of the hand, foot, spine, jaw, or pelvis. Tight joint spaces or interfering bony or soft tissue structures may be dealt with by increasing the size of the surgical incision, performing more extensive dissection to increase exposure of the surgical site, or using retractors or other tools to move interfering structures out of the way, but these techniques increase surgical trauma to the joint, increase the risk of collateral damage beyond that essential to the arthroplasty procedure, and may destabilize the reconstructed joint.

There is a need for reamers adapted for use in tight joint spaces, which would need little to no joint distraction, dissection, retraction, or exposure. This disclosure presents four reamers, each adapted for use in tight joint spaces by having an offset shaft arrangement.

Other objectives and advantages of this technology will become apparent from the following description taken in conjunction with the accompanying drawings which illustrate examples of this technology. The drawings constitute a part of this specification and include examples of the present technology and illustrate various objects and features thereof.

BRIEF DESCRIPTION OF THE DRAWINGS

While examples of the present technology are shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is to be defined by the following claims, along with the full range of equivalents to which such claims are entitled.

Identical reference numerals do not necessarily indicate an identical structure. Rather, the same reference numeral may be used to indicate a similar feature or a feature with similar functionality. Not every feature of each example is labeled in every figure in which that example appears, in order to keep the figures clear. Similar reference numbers (e.g., those that are identical except for the first numeral) are used to indicate similar features in different examples.

DETAILED DESCRIPTION

Figure 1A:
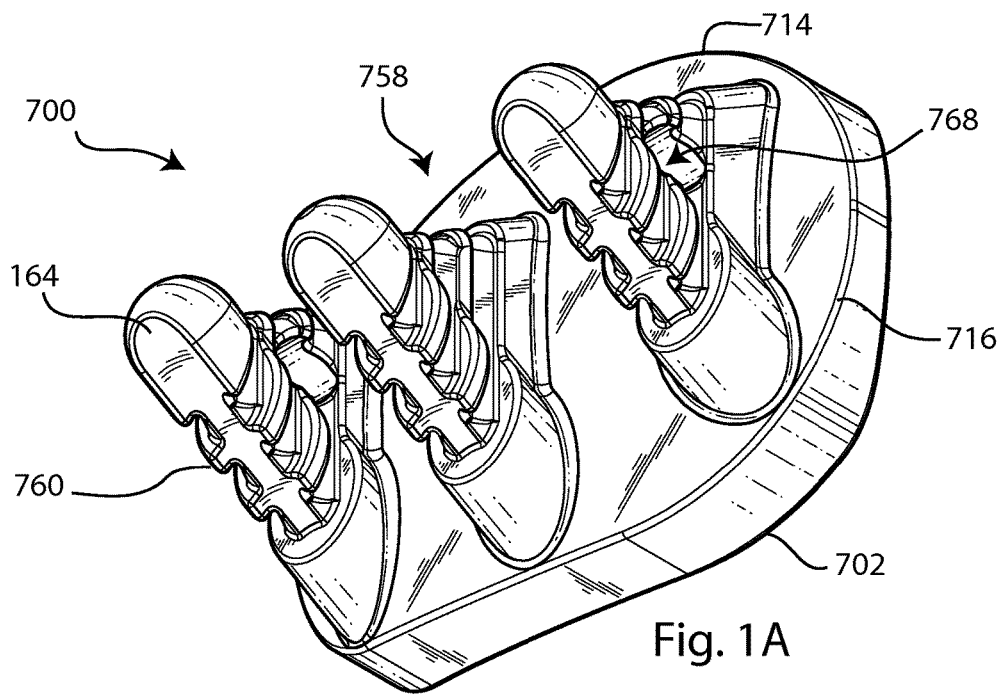
FIG. 1A is an inferior-anterior-medial view of yet another glenoid component.
Figure 1B:
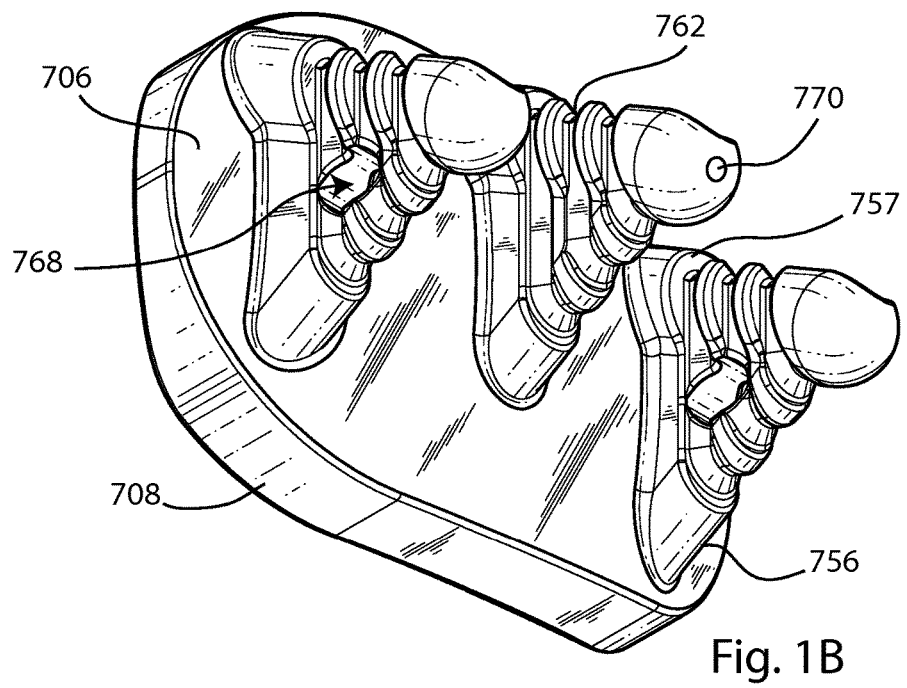
FIG. 1B is an inferior-posterior-medial view of the glenoid component of FIG. 1A.
Figure 1C:
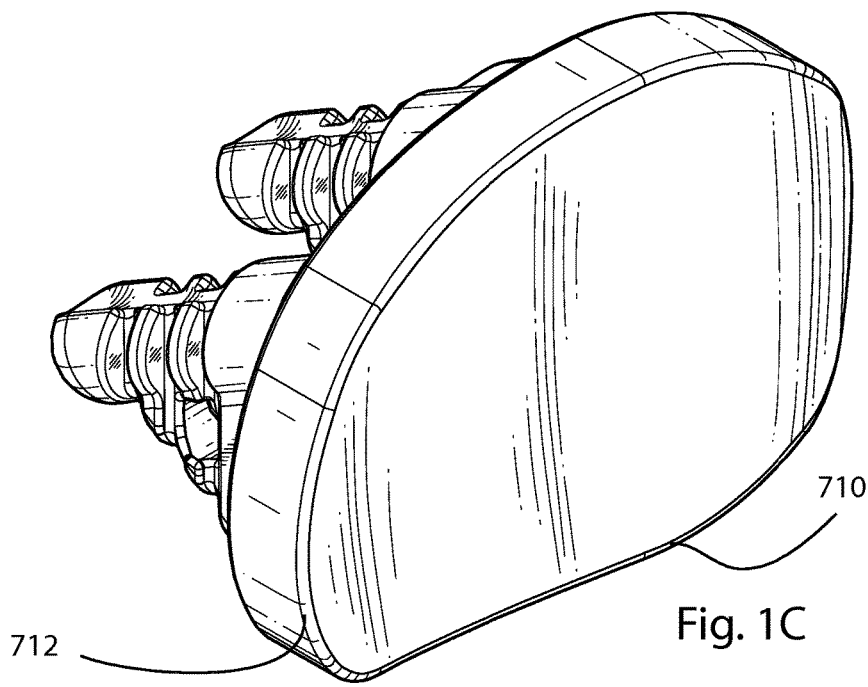
FIG. 1C is a superior-anterior-lateral view of the glenoid component of FIG. 1A.
Figure 1D:
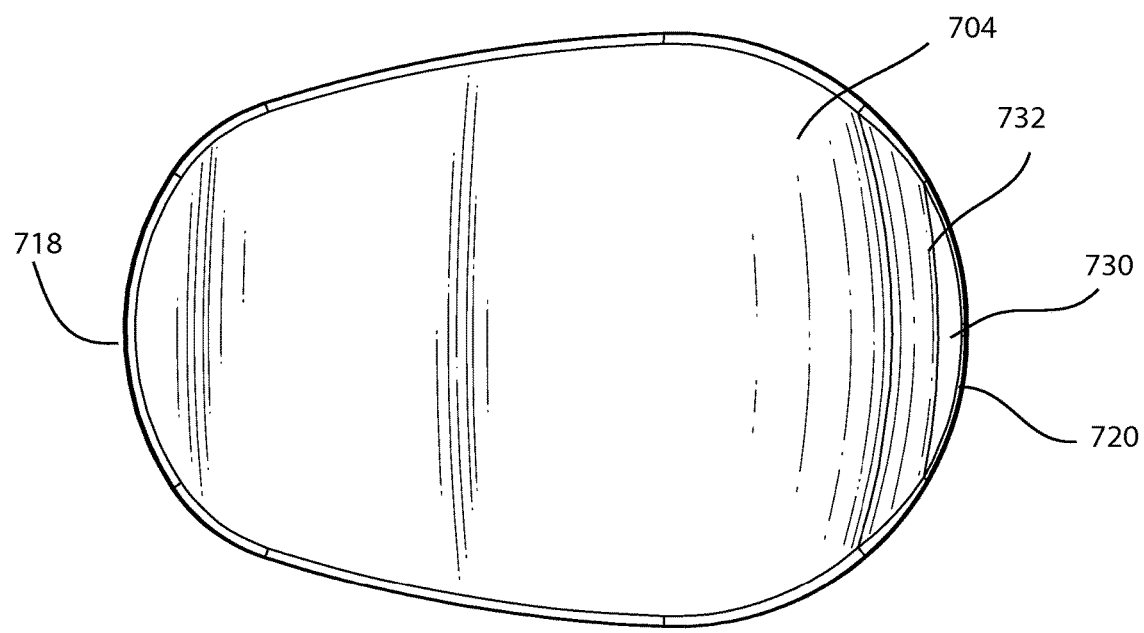
FIG. 1D is a lateral view of the glenoid component of FIG. 1A.
Figure 1E:
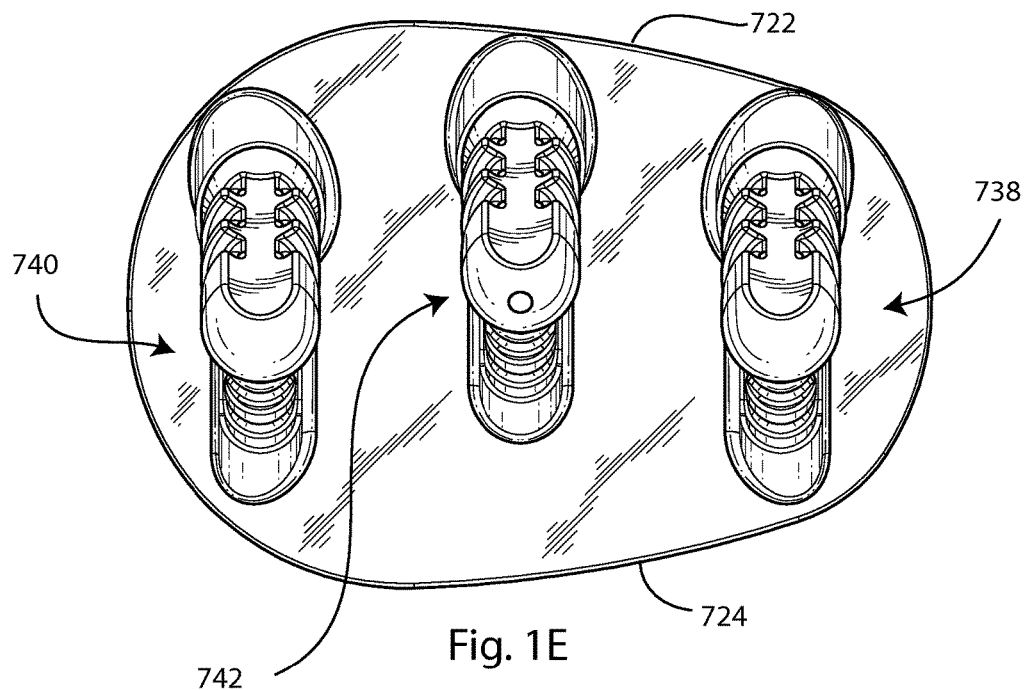
FIG. 1E is a medial view of the glenoid component of FIG. 1A.
Figure 1F:
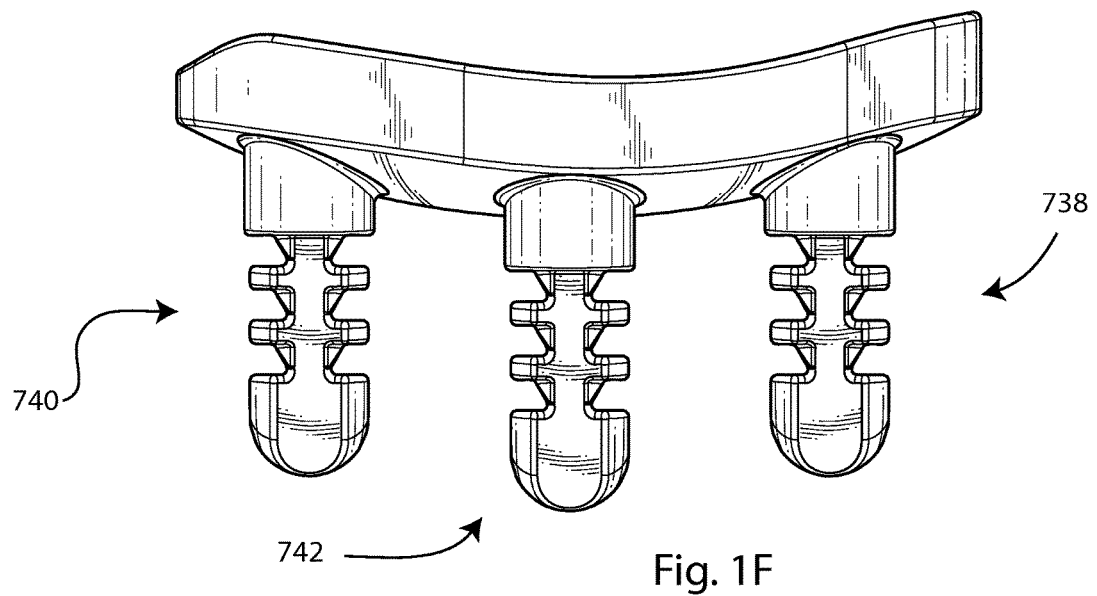
FIG. 1F is an anterior view of the glenoid component of FIG. 1A.
Figure 1G:
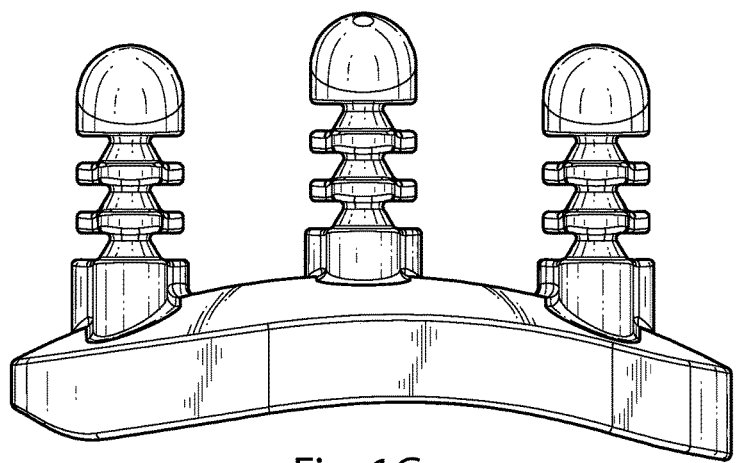
FIG. 1G is a posterior view of the glenoid component of FIG. 1A.
Figure 1H:
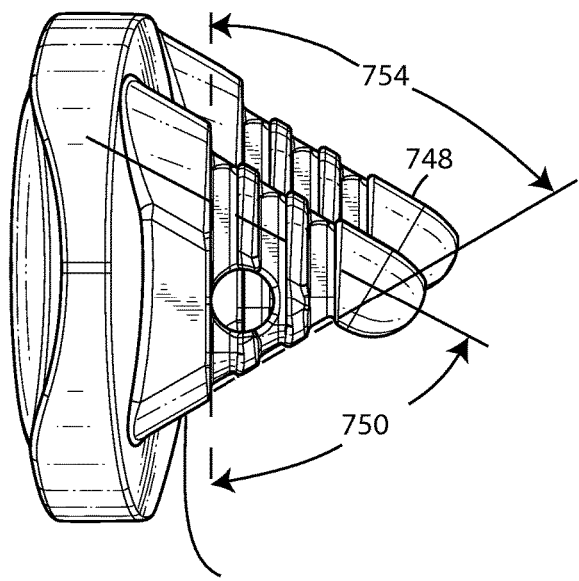
FIG. 1H is an inferior view of the glenoid component of FIG. 1A.
Figure 1I:
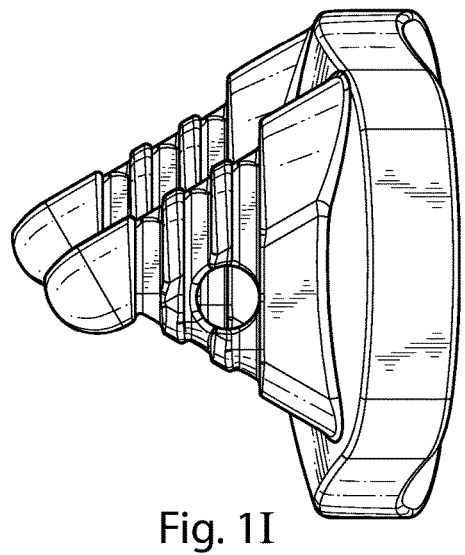
FIG. 1I is a superior view of the glenoid component of FIG. 1A.
Figure 1J:
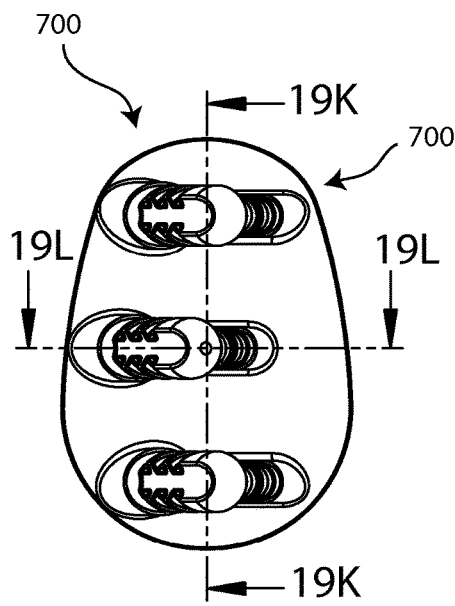
FIG. 1J is a medial view of the glenoid component of FIG. 1A.
Figure 1K:
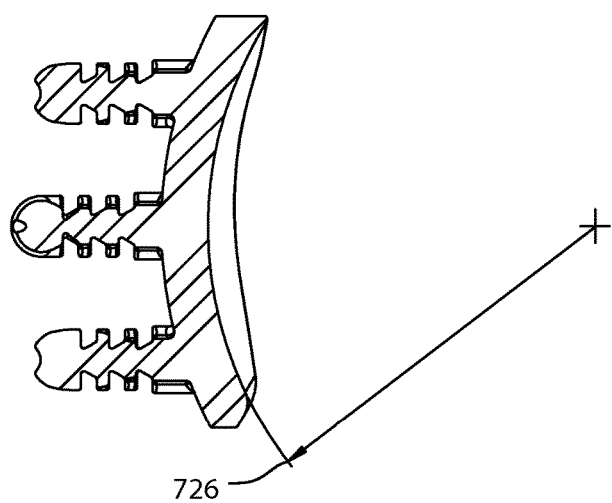
FIG. 1K is a cross sectional view of the glenoid component of FIG. 1J, taken along section line 1K-1K of FIG. 1J.
Figure 1L:
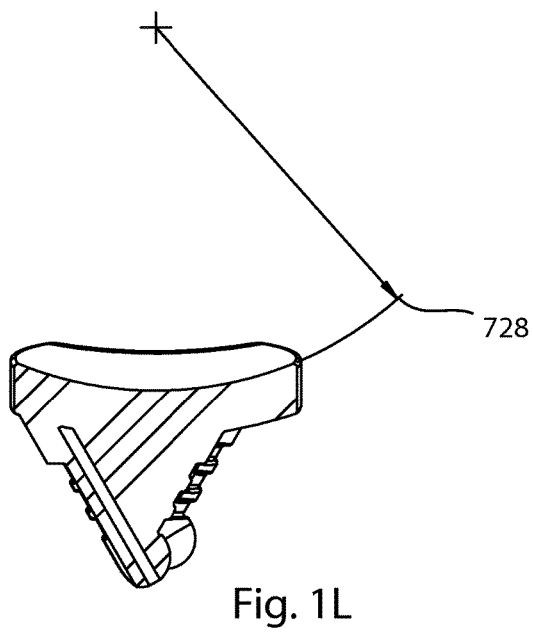
FIG. 1L is a cross sectional view of the glenoid component of FIG. 1J, taken along section line 1L-1L of FIG. 1J.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative exemplary of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

FIGS. 1-6, and the corresponding description below, come from U.S. patent application Ser. No. 14/042,258, which is incorporated herein by reference in its entirety.

Referring to FIGS. 1A-1L, a glenoid component 700 includes a body 702 with a lateral articular surface 704 and an opposite medial bone-facing surface 706. Glenoid component 700 includes the following features, which may be substantially similar to, or the same as, the corresponding features of glenoid component 100 of U.S. patent application Ser. No. 14/042,258: peripheral wall 708, lateral peripheral edge 710, lateral peripheral relief 712, medial peripheral edge 714, medial peripheral relief 716, superior portion 718, inferior portion 720, anterior portion 722, posterior portion 724, S-I radius of curvature 726, A-P radius of curvature 728, inferior chamfer 730, superior anchoring element 738, inferior anchoring element 740, middle anchoring element 742, dowel or mast 748, mast angle 750, triangular reinforcement plate or sail 752, supplementary angle 754, pedestal 756, face 757, fixation features 758, ridge 760, groove 762, slot 764, flat surface 766, and fenestration 768. Glenoid component 700 also includes a chamfer blend radius 732 and a hole 770. The chamfer blend radius 732 is adjacent to the inferior chamfer 730. The chamfer blend radius 732 is more centrally located than is the inferior chamfer 730. The hole 770 extends lengthwise into the dowel 748 of middle anchoring element 742, and may receive a radiographic marker (not shown). Glenoid component 700 lacks an anterior relief or a posterior relief.

Figure 2A:
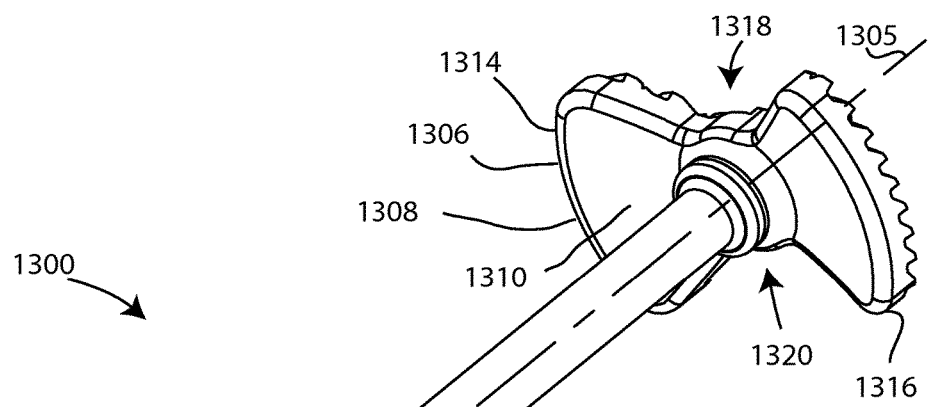
FIG. 2A is an isometric view of a reamer.
Figure 2B:
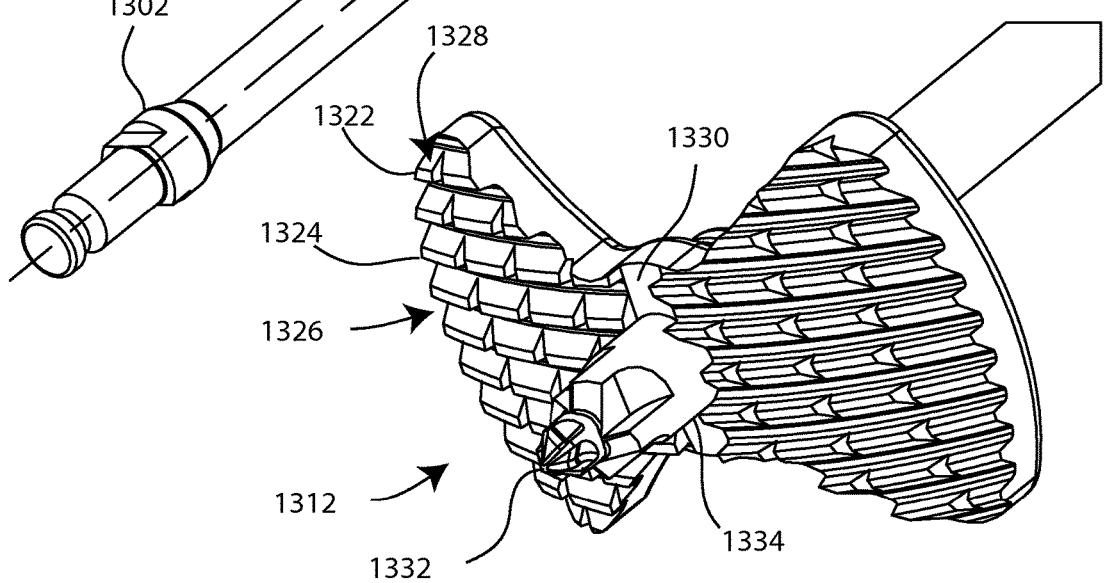
FIG. 2B is another isometric view of a portion of the reamer of FIG. 2A from a different direction.

Referring to FIGS. 2A-2B, a reamer 1300 includes a coupling 1302, a shaft 1304, and a working portion 1306. The coupling 1302 and the working portion 1306 are arranged at opposite ends of the shaft 1304, which is straight in this example. The coupling 1302 connects the reamer 1300 to a torque source, such as a power handpiece or a T-handle, so that the reamer 1300 may be rotated or spun about a central longitudinal axis 1305 of the shaft 1304 by the torque source. The working portion 1306 includes a body 1308 with a first surface 1310 and an opposite bone-facing surface 1312. The bone-facing surface 1312 may match the bone-facing surface 106, 206, 306, 406, 506, 706 of one of the glenoid components disclosed in U.S. patent application Ser. No. 14/042,258. The body 1308 may be described as bi-lobular, the two lobes 1314, 1316 established by opposing indentations 1318, 1320. In other examples, the body 1308 may be round or nearly round. The bone-facing surface 1312 includes bone removal features 1322, which may be teeth, serrations, ridges and grooves, knurling, a sandpaper texture, or the like. In the example shown, the bone removal features 1322 are alternating ridges 1324 and grooves 1326. The cutting edges of the ridges 1324 are interrupted or scored by cross grooves 1328. The bone removal features 1322 on lobe 1314 are oriented opposite to the bone removal features 1322 on lobe 1316 so that the bone removal features 1322 on each lobe 1314, 1316 are oriented to efficiently remove bone as the reamer 1300 spins in one direction. A trough 1330 separates the bone removal features 1322 on lobe 1314 from the bone removal features 1322 on lobe 1316. A drill tip 1332 protrudes from the bone-facing surface 1312. The drill tip 1332 may be end-cutting, side-cutting, or both; an end-cutting example is shown. A second, larger diameter, drill feature 1334 may protrude from the bone-facing surface 1312 around the base of the drill tip 1332. The drill feature 1334 may be end-cutting, side-cutting, or both; an end-cutting example is shown.

Referring now to FIGS. 3-6, a method of using the reamer 1300 to prepare an implantation site for the glenoid components will now be described. One of skill in the art will appreciate that there are many methods for preparing a glenoid to receive the disclosed glenoid components, and that the method shown below represent a few examples of the methods available. Other methods contemplated may include the use of a saw, such as a reciprocating or oscillating saw; a burr, which may be motorized; a punch; an osteotome; and/or a curette, used alone or in combination with one or more drills, guides, and/or cutting jigs. These tools may be used to prepare the glenoid to receive one or more dowels and/or reinforcement plates. Furthermore, while the illustrated method and corresponding instruments include three anchoring elements, in other examples of the technology, the method and corresponding instruments include one or more anchoring elements corresponding to the number and location of the anchoring elements that are present on the selected glenoid prosthetic component.

Figure 3:
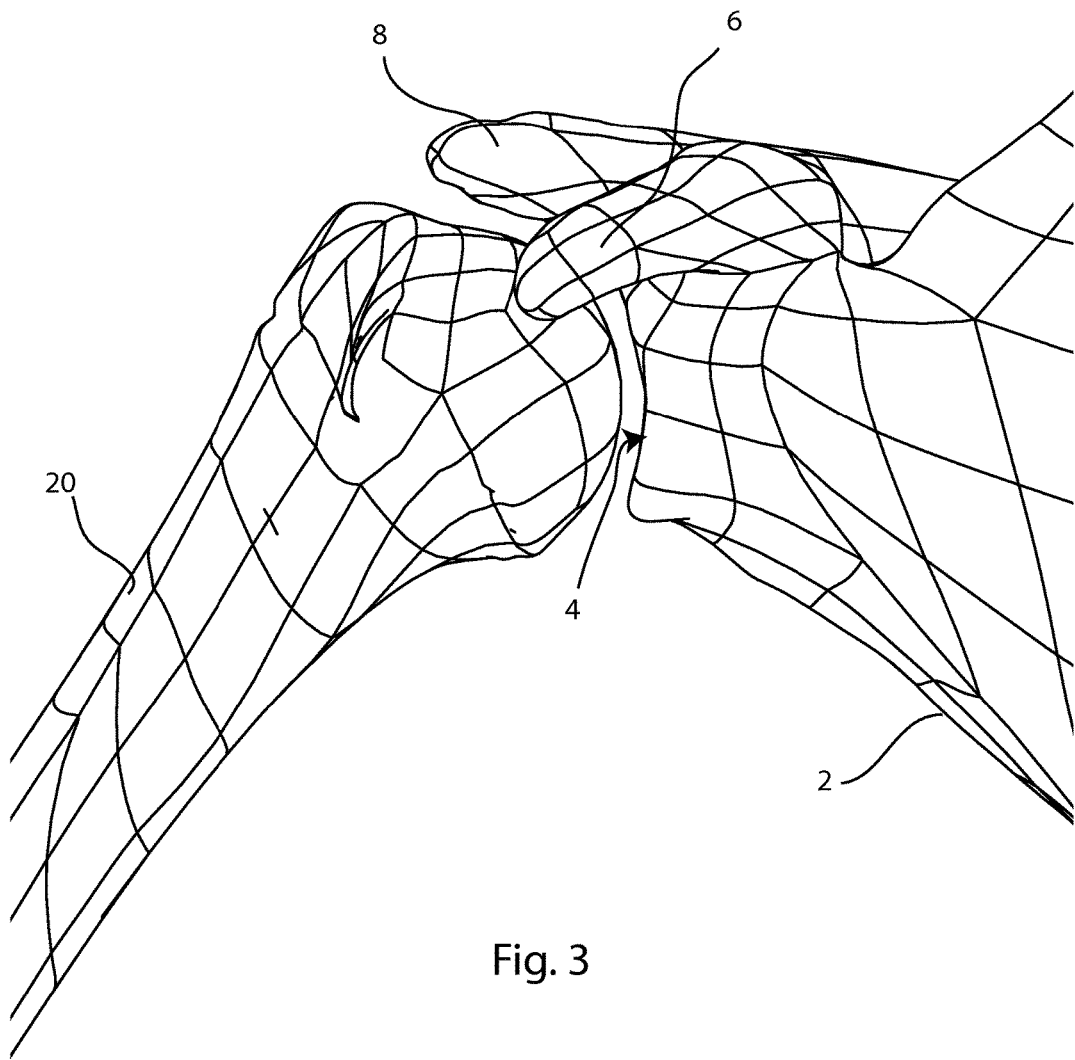
FIG. 3 is an anterior view of a right shoulder joint with a scapula and a humerus.

FIG. 3 illustrates a normal intact right shoulder joint including a scapula 2 and a humerus 20. The scapula includes a glenoid fossa 4, a coracoid process 6, and an acromion process 8.

Figure 4:
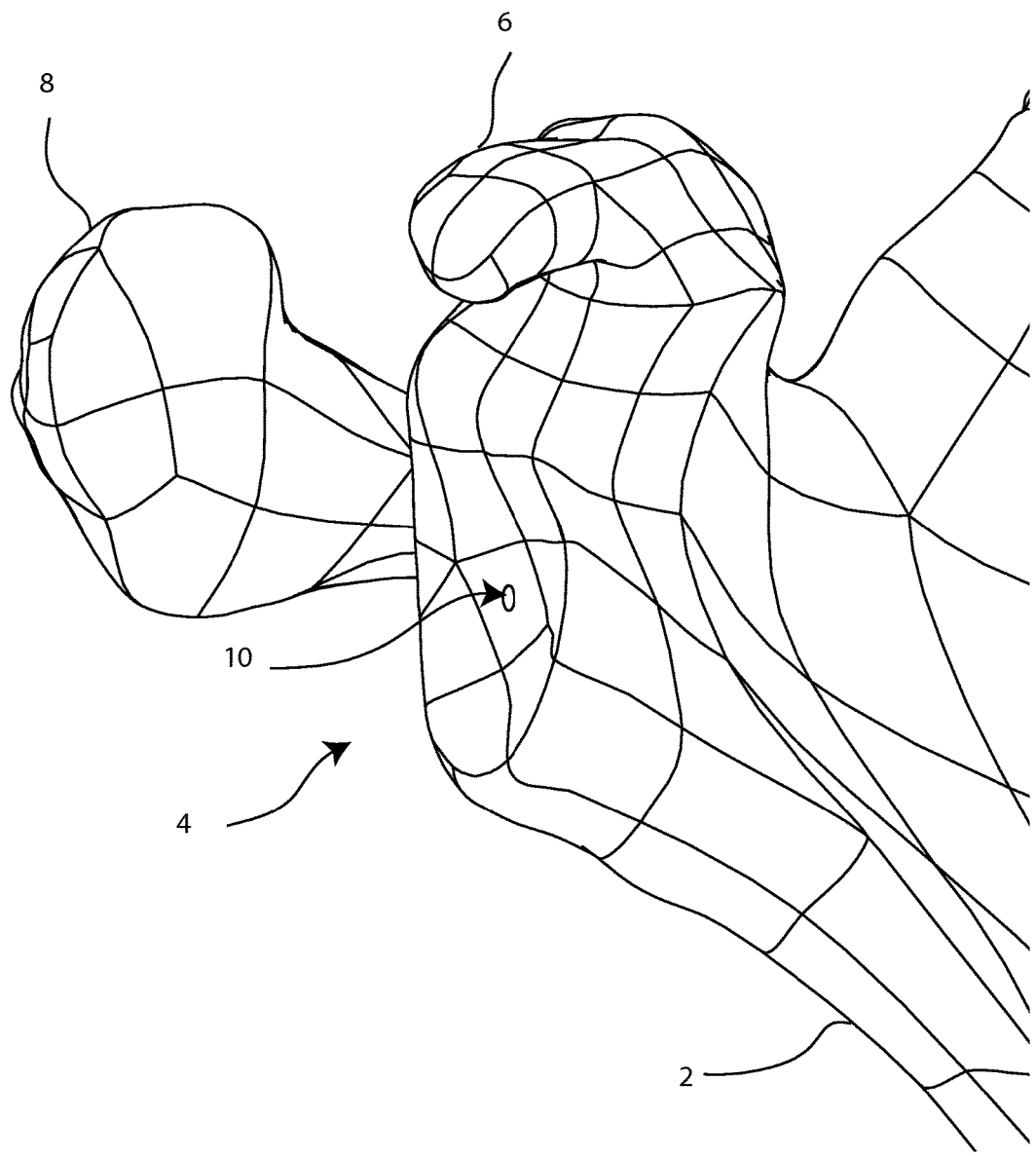
FIG. 4 is an isometric view of the scapula of FIG. 3 after sizing.

FIG. 4 illustrates the step of forming a pilot hole 10 in the glenoid fossa. A small drill or reamer (not shown) may be used freehand at this point to expand the pilot hole 10.

Figure 5:
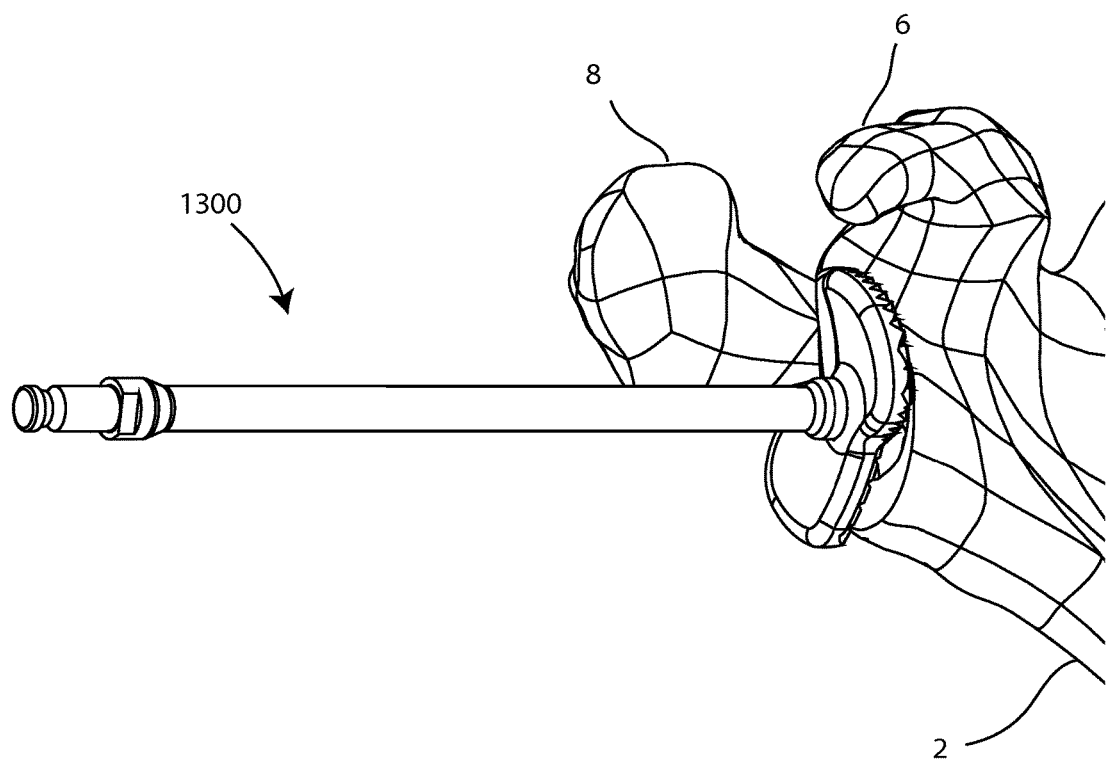
FIG. 5 is an isometric view of the scapula of FIG. 3 with the reamer of FIG. 2A.
Figure 6:
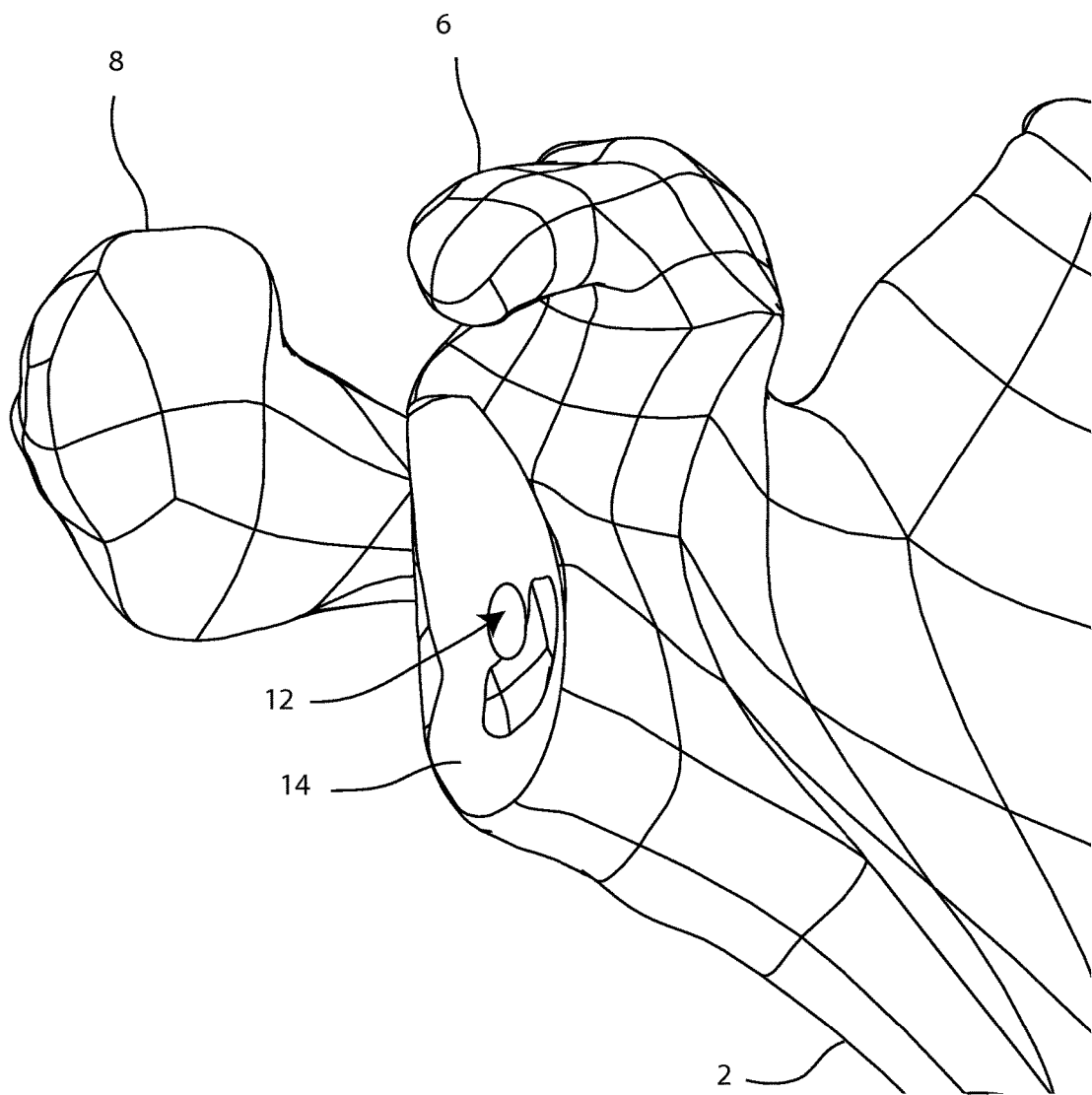
FIG. 6 is an isometric view of the scapula of FIG. 3 after reaming.

FIG. 5 illustrates the step of reaming the glenoid fossa with the reamer 1300. The reamer 1300 may be insinuated between the humeral head and the glenoid fossa 2 by first engaging the drill tip 1332 in the pilot hole 10 with one of the indentations 1318, 1320 cradling the humeral head. The reamer shaft 1304 may be inclined at an acute angle with respect to the glenoid fossa at this point. With the drill tip 1332 in the pilot hole, there is sufficient leverage to push the humeral head posteriorly with the reamer 1300. The reamer shaft 1304 may end up perpendicular to the glenoid fossa at this point. Once the reamer shaft 1304 is properly aligned with the glenoid fossa 4 and the scapula 2, the reamer 1300 may be spun to prepare a reamed surface 14 in the glenoid fossa 4. At the same time, the drill tip 1332 and drill feature 1334, if present, prepare hole 12 in the former location of the pilot hole 10. FIG. 6 shows the scapula 2 after the reaming step.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Coatings may be present. Different materials may be used within a single part. Any component disclosed herein may be colored, coded or otherwise marked to make it easier for a user to identify the type and size of the component, the setting, the function(s) of the component, and the like.

The reamers disclosed herein may be used to prepare a bone bed to receive or support an arthroplasty implant. The prepared bone bed may be smooth. The reamers may also create a central pilot hole; the pilot hole may be used to locate subsequent bone preparation guides and/or tools. The reamers may be designed with various offset shaft arrangements, such as the following examples, to adapt the reamers for use in tight joint spaces where a conventionally designed reamer would meet with interference from body structures. In one example, the disclosed reamers may be used for glenoid preparation in shoulder arthroplasty. In this example, one interfering structure is the humeral head. Of course, the disclosed reamers may also be used in other arthroplasty procedures for other skeletal joints.

In this specification, an axis is a straight line which has infinite length, zero breadth, and zero thickness. An object may rotate about an axis or move along an axis. Two coplanar axes are collinear if they have more than one point in common; in fact, all of their points are in common. Two coplanar axes intersect if they have exactly one point in common. Two coplanar axes are parallel if they have zero points in common. Two non-coplanar axes are skew if they do not intersect and are not parallel; they also have zero points in common.

In this specification, polyaxial means movement which occurs about multiple axes. Polyaxial and multiaxial are synonymous. A ball-and-socket joint is one example of a joint which provides polyaxial movement about a point, a center point of rotation. The range of motion of a polyaxial joint may be conical, wherein the vertex of the cone lies at the center point of rotation of the polyaxial joint. The range of motion of a polyaxial joint may be expressed as the included angle of the cone, or as the half-angle of the cone. The skeleton includes polyaxial joints, such as the shoulder joint and the hip joint.

Design objectives for the disclosed reamers include: prepare a smooth surface of revolution, where the axis of revolution may be perpendicular to the natural bony feature being reamed; minimize contact with surrounding body structures, such as the opposing bone of the joint, so that the reamer is not used as a pry bar to distract the joint; and ease of use equivalent to a conventional straight reamer. Any of the disclosed reamers may prepare the glenoid fossa of the scapula 2 as shown in FIG. 6.

Figure 7:
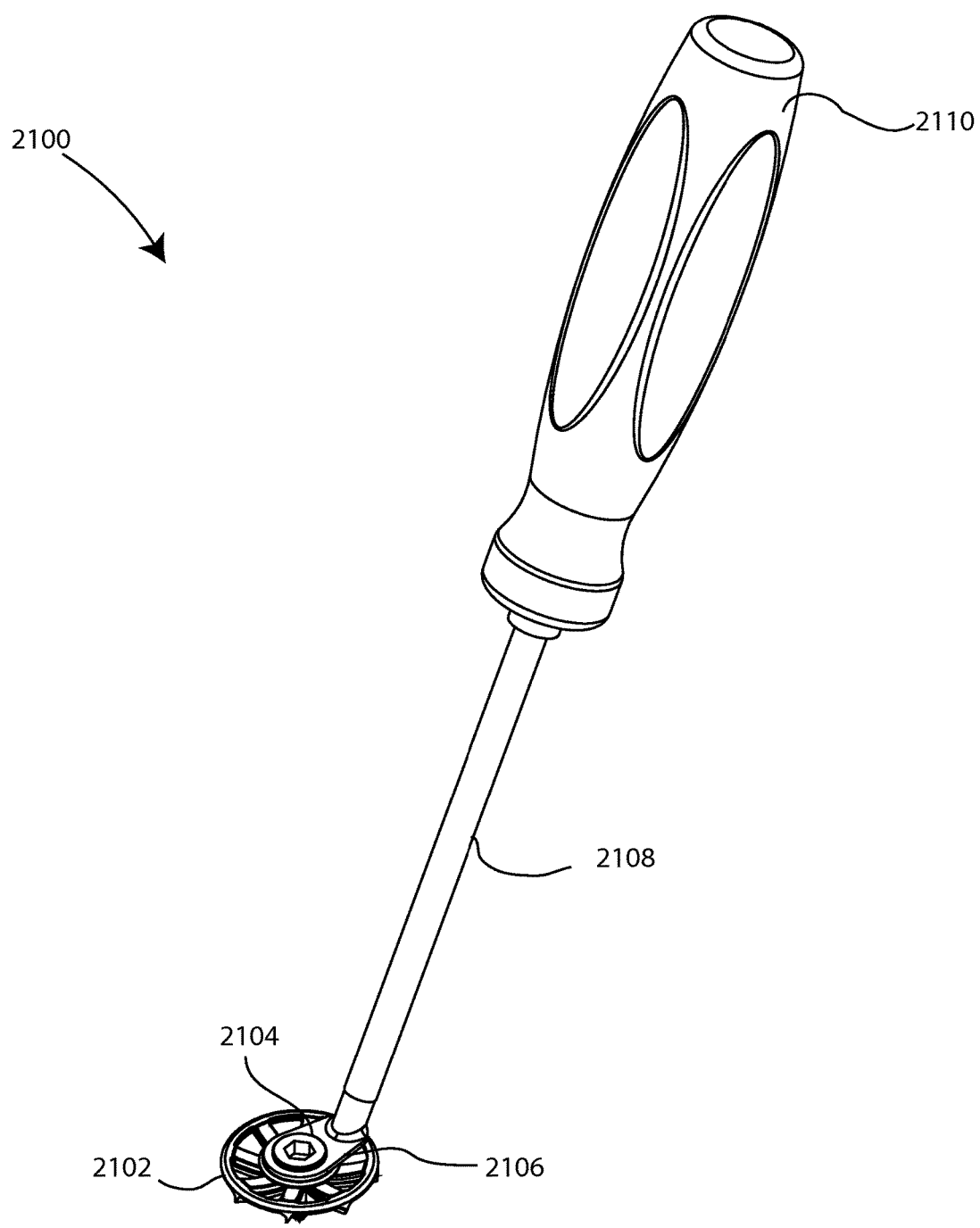
FIG. 7 is an isometric view of an offset reamer.

Referring to FIG. 7, an offset reamer 2100 includes a reamer head 2102, a reamer coupler 2104, a working tip 2106, a shaft 2108, and a handle 2110. FIGS. 7-11 show various views of offset reamer 2100.

Figure 8:
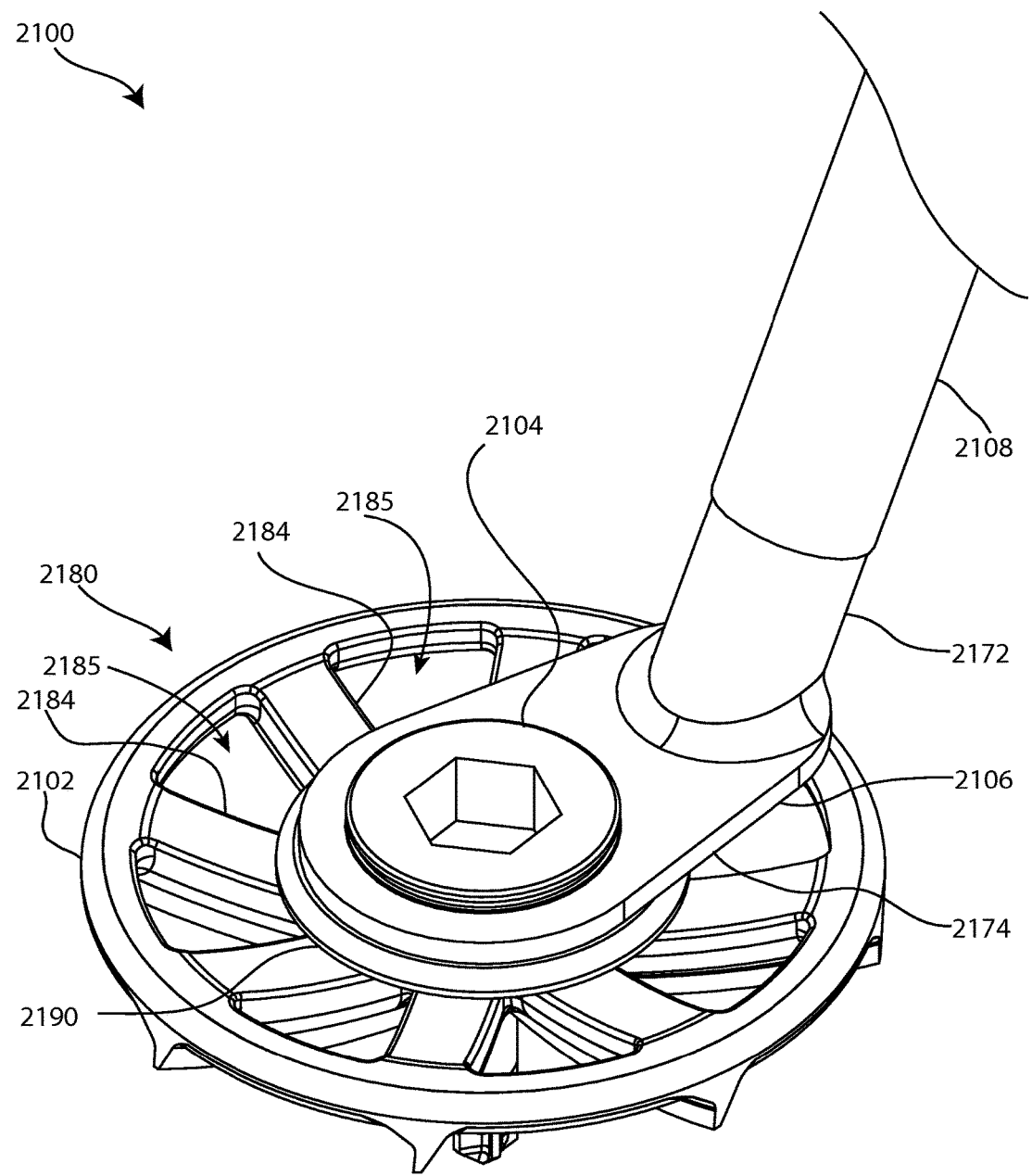
FIG. 8 is an isometric view of a portion of the offset reamer of FIG. 7.
Figure 9:
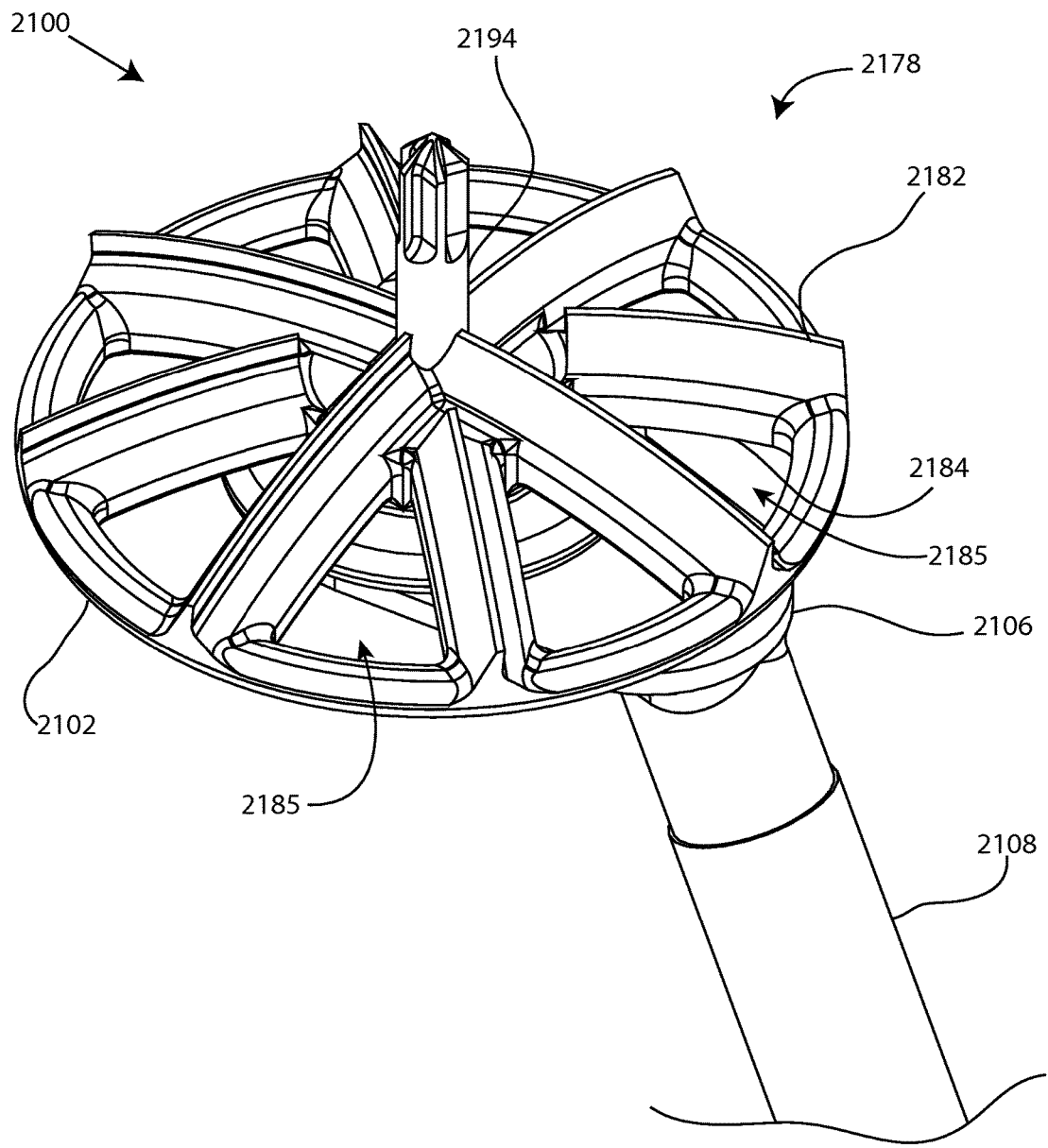
FIG. 9 is an isometric view of a portion of the offset reamer of FIG. 7 from a second viewpoint.

The reamer head 2102 is a round part with a central longitudinal rotational axis 2103, a convex obverse side 2178, or bone-facing side or cutting side (FIG. 9), and a reverse side 2180 (FIG. 8). The obverse side 2178 may be flat or concave in other examples devoted to other joints around the body. The obverse side 2178 includes bone removal features 2182, which may be teeth, serrations, ridges and grooves, knurling, a sandpaper texture, or the like. In the example shown, the bone removal features 2182 are sharpened edges on radial arms 2184 of the reamer head 2102. Eight arms 2184 are shown in the example, although any number of arms may be provided. The arms 2184 in the example are separated by windows 2185 or apertures. In other examples, the reamer head 2102 may share some or all of the characteristics of body 1308 disclosed above. The reamer head 2102 includes a central aperture 2186 (FIGS. 10-11), which may include a drive portion 2189 adjacent to the reverse side 2180 and a circular portion adjacent to the obverse side. The drive portion 2189 may be a hex socket, as illustrated in FIG. 10, or another configuration for torque transmission in at least one rotational direction.

Figure 10:
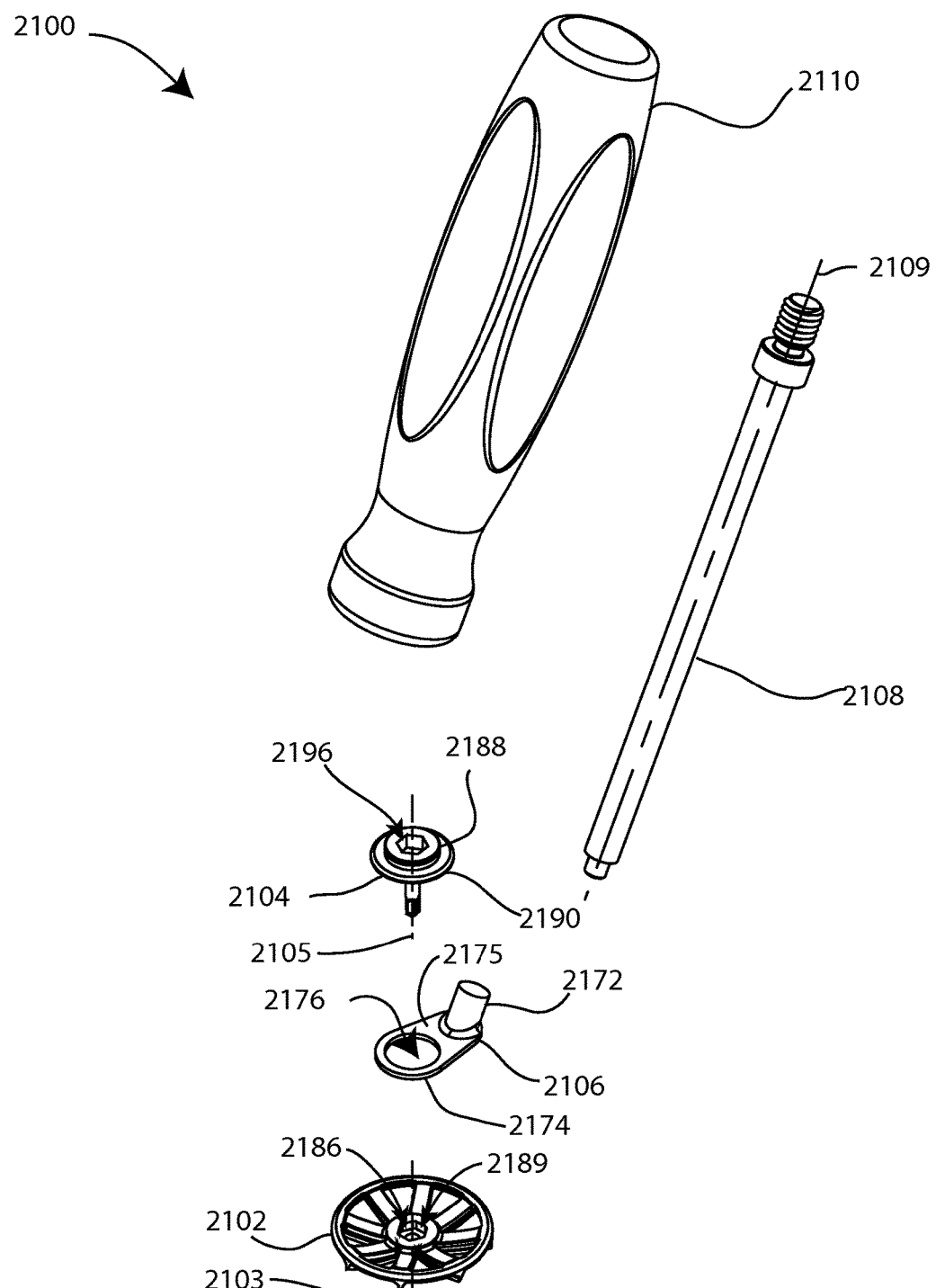
FIG. 10 is an isometric exploded view of the offset reamer of FIG. 7.
Figure 11:
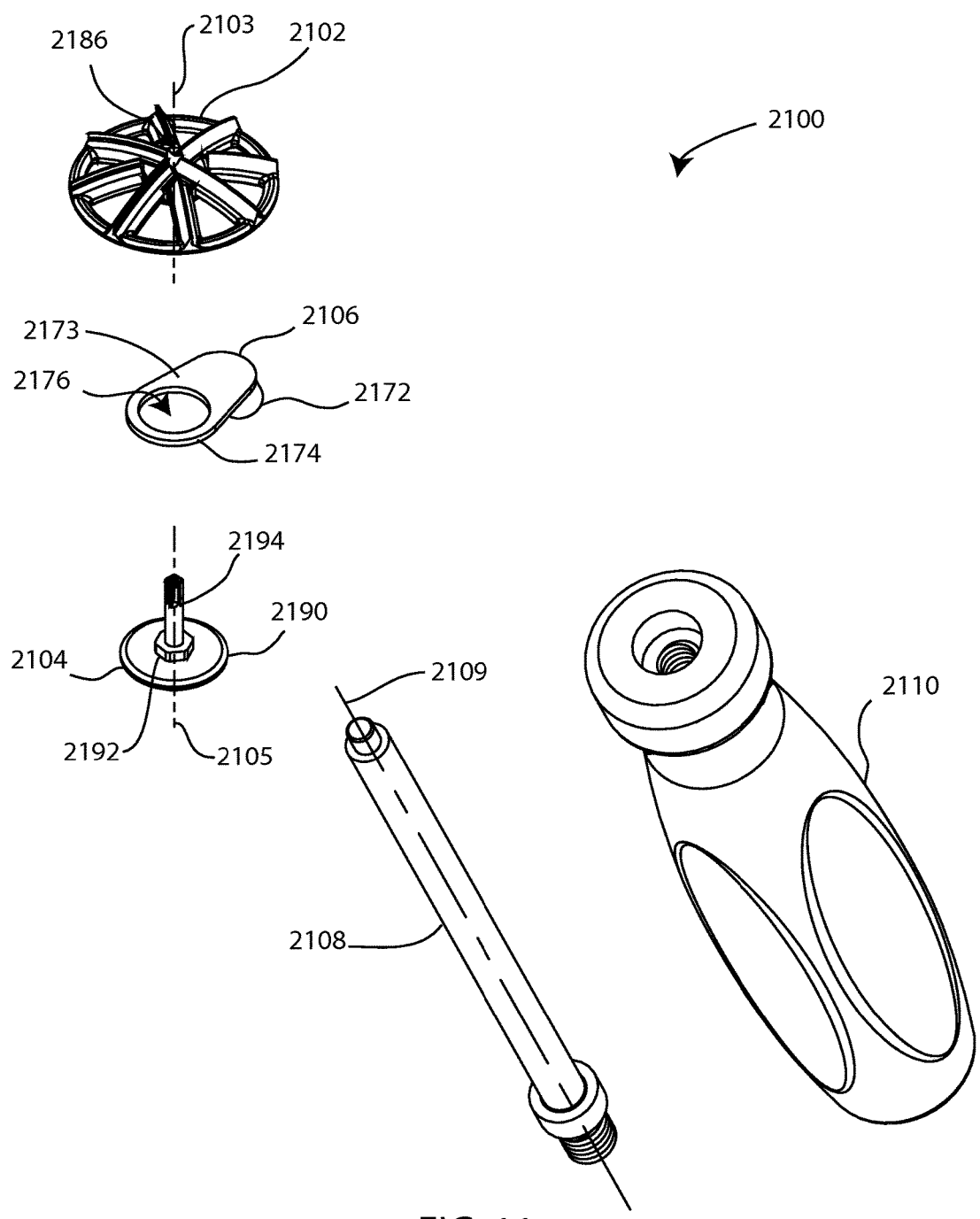
FIG. 11 is an isometric exploded view of the offset reamer of FIG. 7 from a second viewpoint.

Referring to FIGS. 10-11, the reamer coupler 2104 includes a central longitudinal rotational axis 2105, a head 2188, a flange 2190 under the head, a drive feature 2192 under the flange, and a shaft 2194 under the drive feature. The reamer coupler 2104 may be referred to as a coupling which connects the offset reamer 2100 to a prime mover or torque source such as a power driver or T-handle so that the reamer head 2102 may be rotated or spun about the axis 2103. The head 2188 may include a drive portion 2196, which may be a hex socket, as illustrated in FIG. 10, or another configuration for torque transmission in at least one rotational direction. The drive feature 2192 may be a hex key, as illustrated in FIG. 11, or another configuration for cooperation with the drive portion 2189 of the aperture 2186 of the reamer head 2102 for torque transmission in at least one rotational direction. The shaft 2194 may include cutting flutes at least along the leading tip, and may therefore be called a drill tip. FIG. 11 illustrates this configuration. The shaft 2194 may be spring loaded, and may be biased to be normally extended or normally retracted. In the latter situation, the shaft 2194 may only extend outwardly when a driver (discussed below) is engaged with the drive portion 2196.

The working tip 2106 may be coupled to one end of the shaft 2108 and the handle 2110 may be coupled to the other end of the shaft 2108 to form a handle assembly. The working tip 2106, the shaft 2108, and the handle 2110 may be permanently or temporarily coupled together. For example, the working tip 2106 and/or handle 2110 may be permanently welded to the shaft 2108. Alternatively, the working tip 2106 and/or handle 2110 may be temporarily threaded or snapped to the shaft 2108. The working tip 2106 includes a shaft portion 2172 for connection to the shaft 2108 and a plate portion 2174 that extends obliquely from the shaft portion. The shaft 2108 includes a central longitudinal axis 2109, with which the shaft portion 2172 aligns when the shaft 2108 and the shaft portion 2172 are connected. The plate portion 2174 includes an obverse side 2173, or bone-facing side, and a reverse side 2175 opposite the bone-facing side. The plate portion is pierced by an aperture 2176 or hole which may extend through the obverse side 2173 and the reverse side 2175.

The reamer head 2102, the reamer coupler 2104, and the working tip 2106 are operatively assembled by inserting the head 2188 through the aperture 2176 so that the flange 2190 contacts the bone-facing side 2173 of the plate portion 2174, and inserting the shaft 2194 through the circular portion of the aperture 2186 of the reamer head 2102 so that the drive feature 2192 engages the drive portion of the aperture 2186 of the reamer head 2102; in the illustrated example, this involves inserting the hex key 2192 into the hex socket drive portion 2189 of aperture 2186. The working tip 2106 may be said to carry the reamer coupler 2104 and the reamer head 2102. The head 2188, the plate portion 2174, the shaft 2194, the drive feature 2192, and/or the aperture 2186 may include a retention element, such as a ball detent, clip, retaining ring, groove, taper, twist, or the like, to keep the head 2188, the plate portion 2174, the shaft 2194, the drive feature 2192, and/or the aperture 2186 coupled together until intentionally disassembled. The operative assembly of the reamer head 2102, the reamer coupler 2104, and the working tip 2106 may be referred to as a working portion of the offset reamer 2100.

When the reamer head 2102, the reamer coupler 2104, and the working tip 2106 are operatively assembled, at least the reamer head 2102 and the reamer coupler 2104 may be rotationally coupled or fixed together with axes 2103, 2105 collinear. Together, the reamer head 2102 and the reamer coupler 2104 may rotate freely relative to the working tip 2106 about axis 2103. The handle assembly of the working tip 2106, the shaft 2108, and the handle 2110 may be manipulated by a user to control the location and orientation of the reamer axis 2103.

A driver, such as the reamer driver 2216 shown in FIGS. 12-17, may include a Hudson connector or torque bit which couples to a prime mover or torque source, such as a power driver or a T-handle. The tip of the driver may be directly engaged with the reamer coupler 2104, and the driver may be rotated by the prime mover about a central longitudinal rotational axis of the driver, or driver axis, to turn the reamer coupler 2104 and the reamer head 2102 about axis 2103. In other words, the driver may be rotationally coupled to the reamer coupler 2104 and the reamer head 2102. For example, the driver may have a straight hex key drive tip to engage the hex socket drive portion 2196 so that the driver axis is in line with, or coaxial with, the axis 2103. The driver may alternatively have a ball drive tip, such as the ball hex key drive tip 2220 shown in FIGS. 12-17, which permits the driver axis to be polyaxially obliquely angled, or polyaxially angularly offset, relative to the rotational axis 2103 of the reamer head 2102 in the manner discussed below for offset reamer 2200. In this example with the ball hex key drive tip, the driver axis may be described as being angularly offset from, or noncollinear with, the rotational axis 2103 of the reamer head 2102, so that the driver axis and the axis 2103 have no more than a single mathematical point in common, and that only if the driver axis and the axis 2103 intersect. Therefore, the driver may be referred to as an offset driver or an offset drive shaft due to the unconstrained angular offset between the driver axis and the rotational axis 2103 of the reamer head 2102. The driver may alternatively include other adaptations to permit the driver to be obliquely angled, or angularly offset, relative to the rotational axis 2103 of the reamer head 2102, such as a universal joint, a flexible shaft portion, a bevel gear acting against the reamer head 2102 and/or the reamer coupler 2104, a ball Torx drive (hexalobular), a ball star drive, or various other ball polygonal or polylobular design. More specifically, the driver may have a ball drive tip with five or more corners or points, which may provide a smooth feel with less turbulence or kicking during actuation. While the ball hex key drive tip is an example which provides polyaxial angular offset, other examples may provide a fixed angular offset. In use, the driver may be angularly repositioned relative to the axis 2103 at any time the user desires, whether or not the driver is being actuated or rotated. The driver may be repositioned independently of any manipulation of the reamer head axis 2103 or the handle assembly, so that the angular offset between the axis 2103 and the driver axis is continuously variable.

Figure 12:
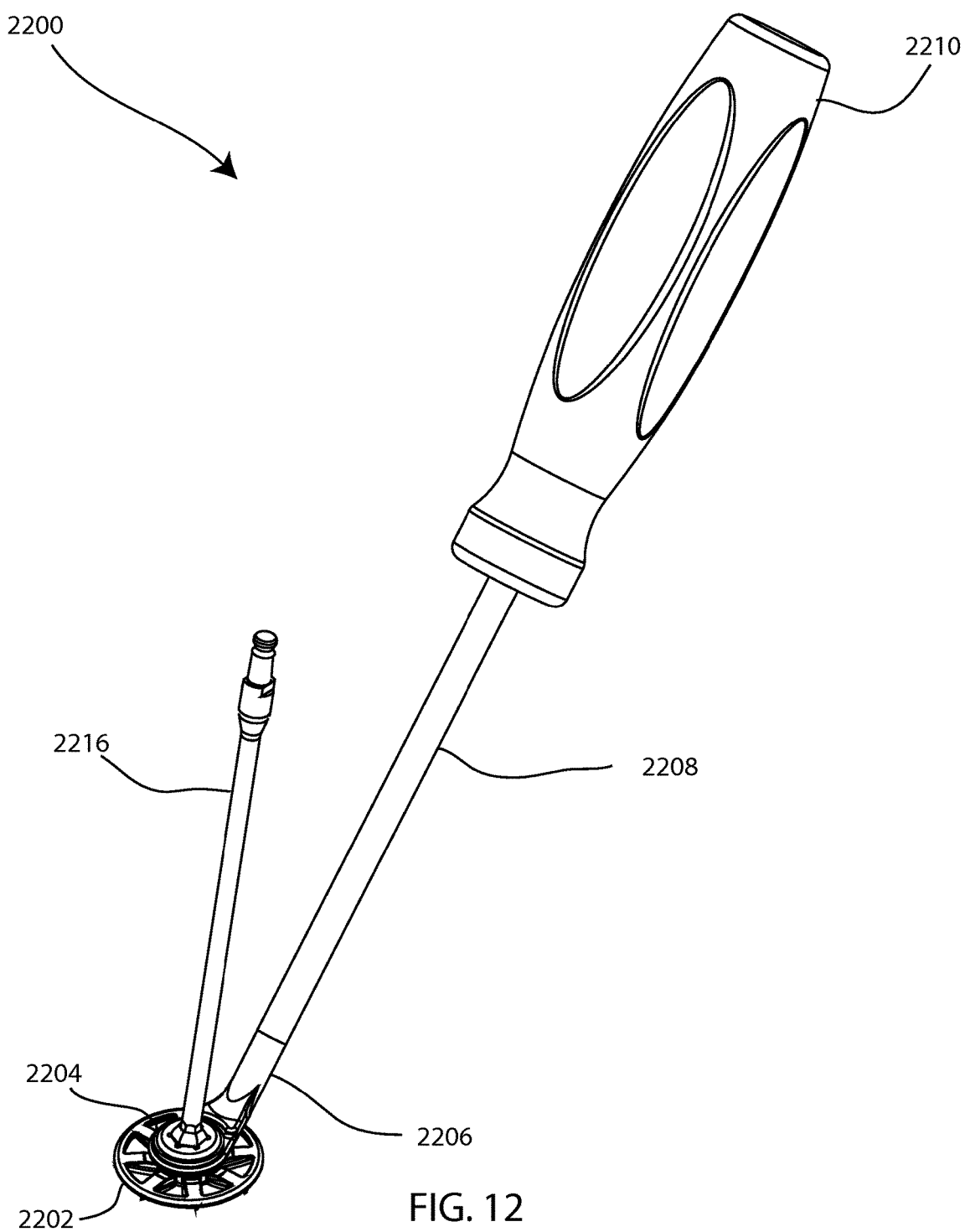
FIG. 12 is an isometric view of another offset reamer.

Referring to FIG. 12, another offset reamer 2200 includes a reamer head 2202, a reamer coupler 2204, a working tip 2206, a shaft 2208, and a handle 2210. FIGS. 12-17 show various views of offset reamer 2200. Offset reamer 2200 also includes a first bushing 2212 and a second bushing 2214, which are seen best in FIGS. 13-16. Offset reamer 2200 is shown with a reamer driver 2216, which may be used interchangeably with offset reamers 2100, 2200.

Figure 13:
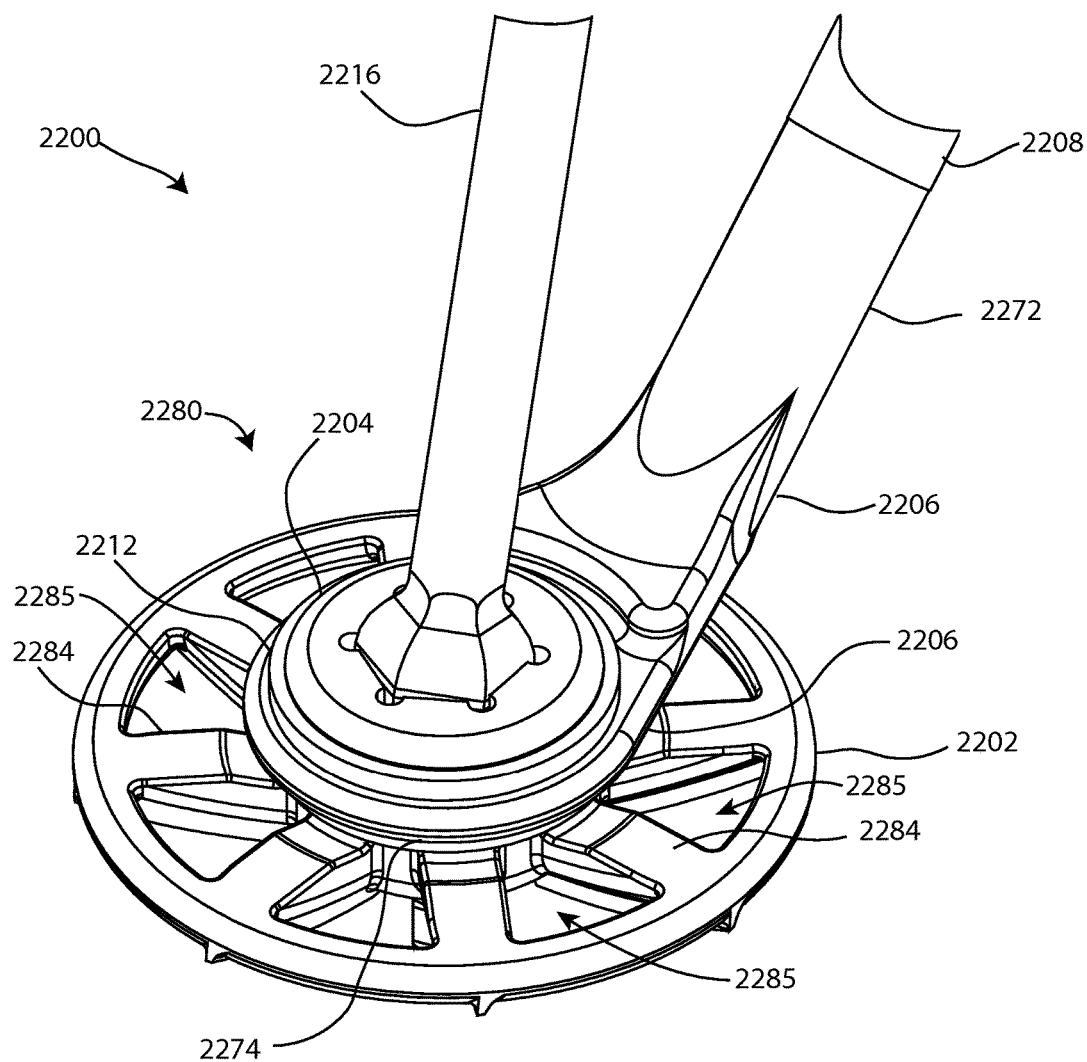
FIG. 13 is an isometric view of a portion of the offset reamer of FIG. 12.
Figure 14:
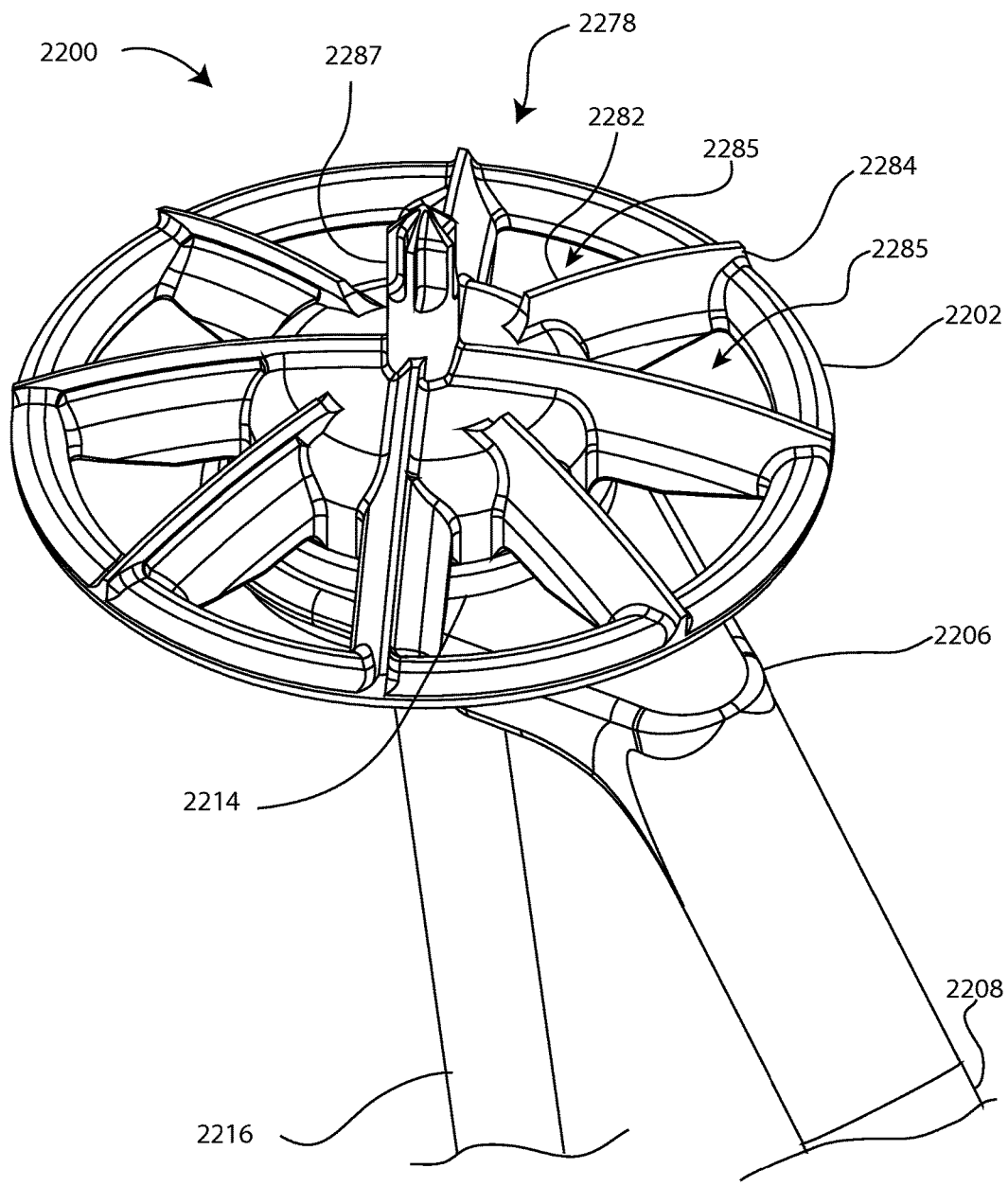
FIG. 14 is an isometric view of a portion of the offset reamer of FIG. 12 from a second viewpoint.
Figure 15:
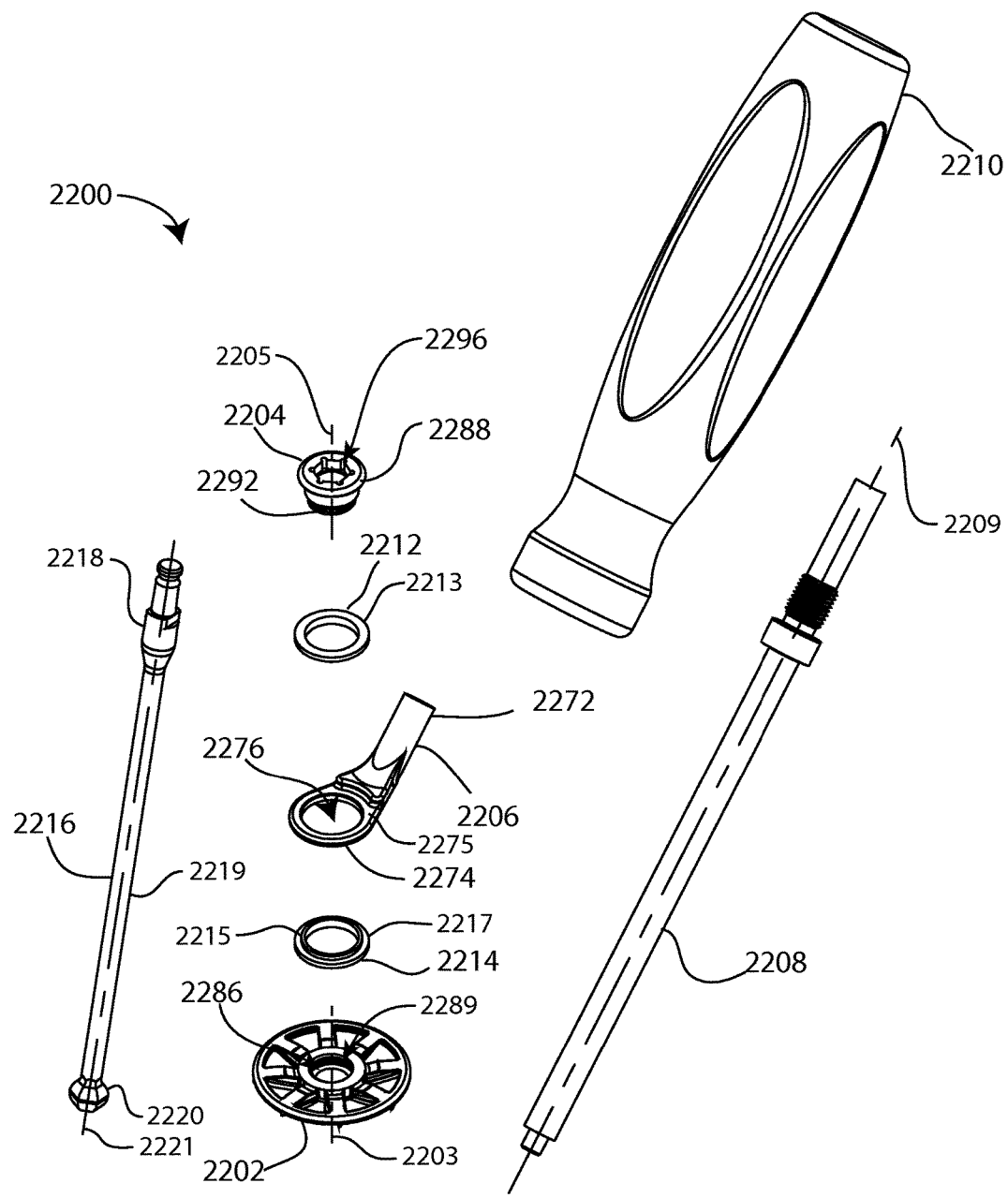
FIG. 15 is an isometric exploded view of the offset reamer of FIG. 12.
Figure 17:
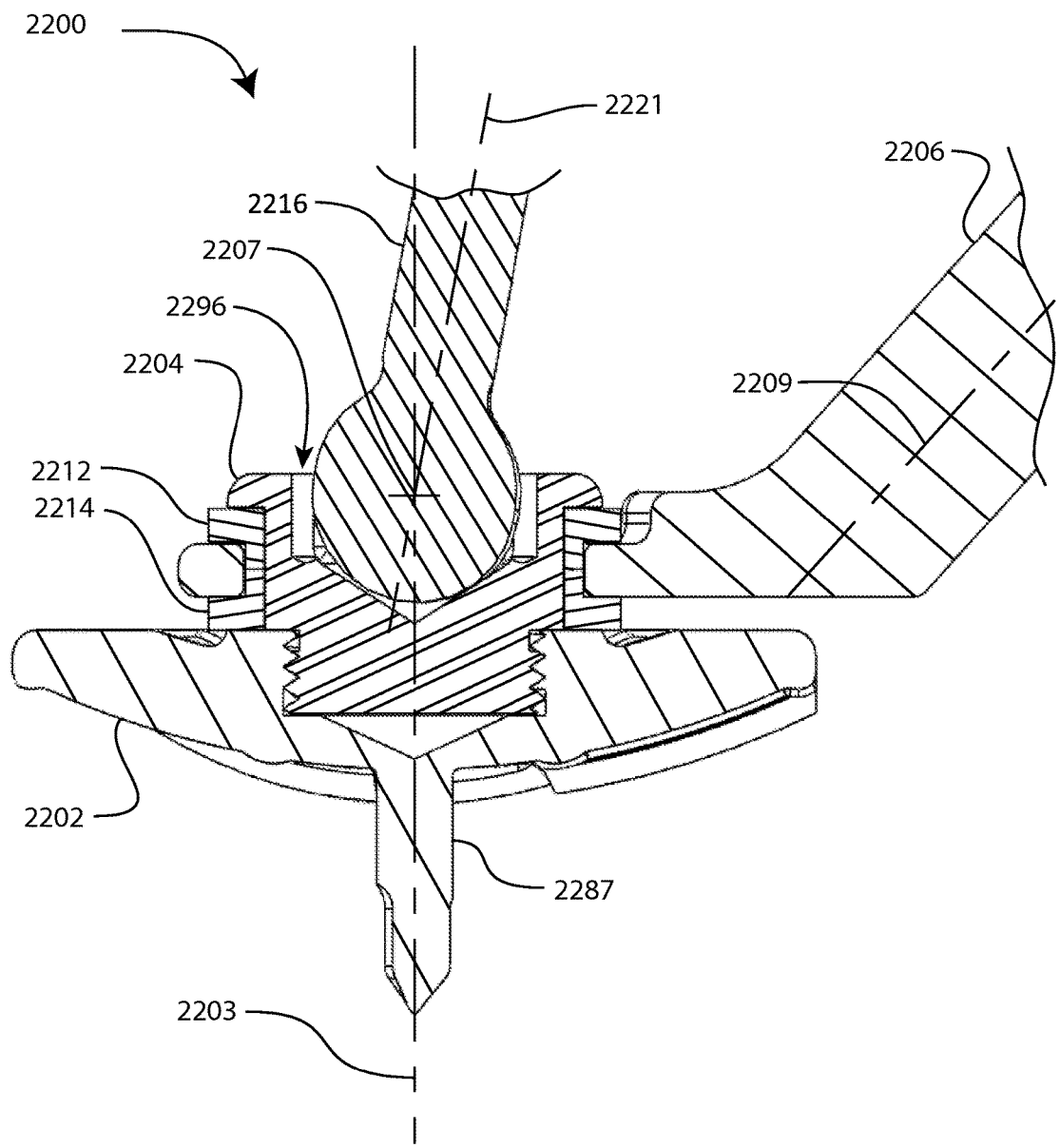
FIG. 17 is a cross sectional view through a portion of the offset reamer of FIG. 12.

The reamer head 2202 is a round part with a central longitudinal rotational axis 2203, a convex obverse side 2278, or bone-facing side or cutting side (FIG. 14), and a reverse side 2280 (FIG. 13). The obverse side 2278 may be flat or concave in other examples devoted to other joints around the body. The obverse side 2278 includes bone removal features 2282, which may be teeth, serrations, ridges and grooves, knurling, a sandpaper texture, or the like. In the example shown, the bone removal features 2282 are sharpened edges on radial arms 2284 of the reamer head 2202. Eight arms 2284 are shown in the example, although any number of arms may be provided. The arms 2284 in the example are separated by windows 2285 or apertures. In other examples, the reamer head 2202 may share some or all of the characteristics of body 1308 disclosed above. The reamer head 2202 includes a central socket 2286 in the reverse side 2280 (FIG. 15). The central socket 2286 may include a drive portion 2289 adjacent to the reverse side 2280, and may include a circular portion adjacent to the obverse side. The drive portion 2289 may be a threaded socket, as illustrated in FIGS. 15 and 17, or another configuration for torque transmission in at least one rotational direction. The reamer head 2202 is illustrated with a central drill point 2287 protruding from the obverse side 2278. In this example, the central drill point 2287 is integral with the reamer head 2202. Alternately, the central drill point may be separate from the reamer head 2202, and may be integral with the reamer coupler 2204, and may protrude through a circular portion of the central aperture 2286 in the manner described above for reamer head 2102 and reamer coupler 2104. The central drill point 2287 may include cutting flutes at least along the leading tip. The central drill point 2287 may be spring loaded, and may be biased to be normally extended or normally retracted. In the latter situation, the central drill point 2287 may only extend outwardly when a driver (discussed below) is engaged with the reamer coupler 2204.

Figure 16:
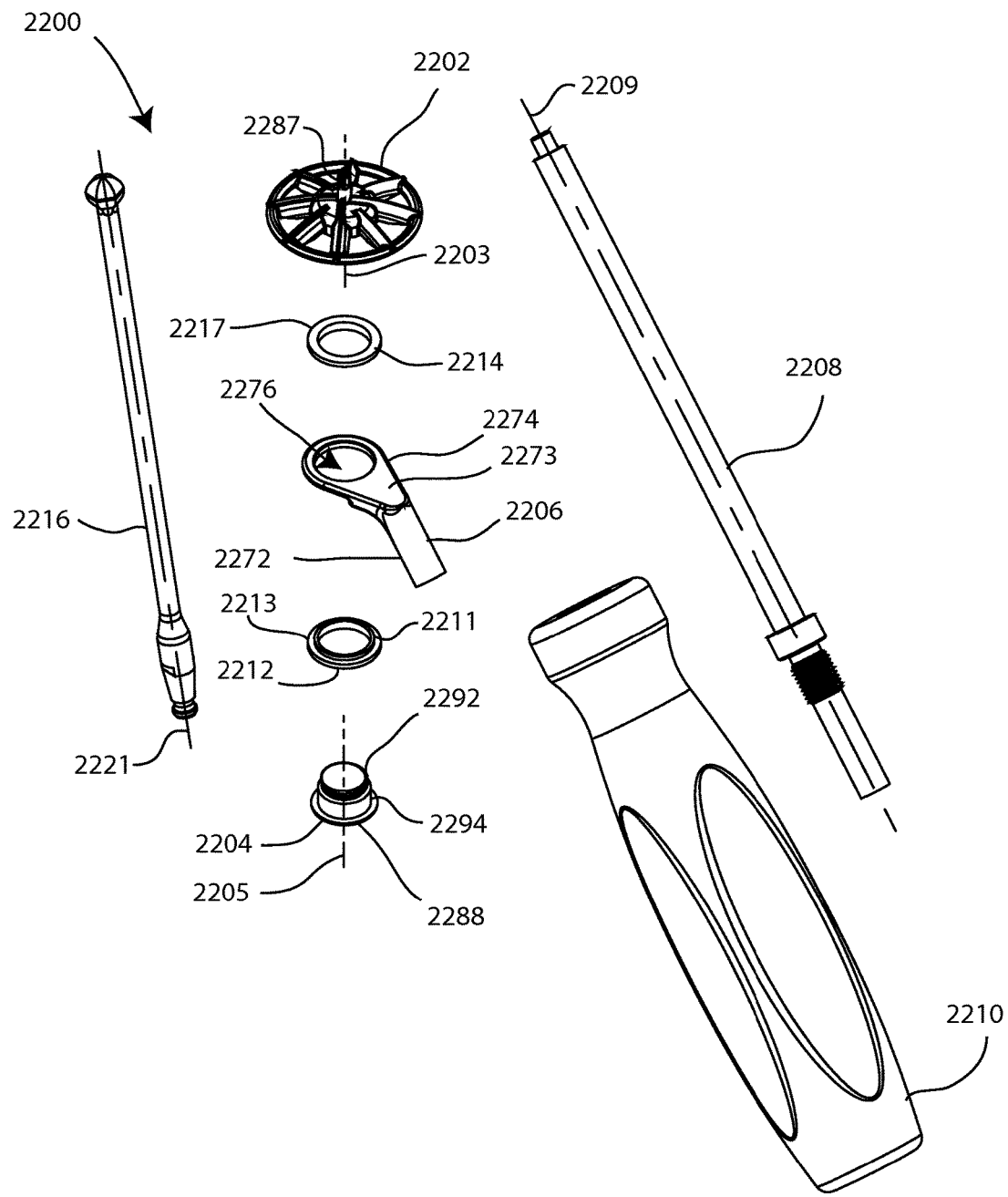
FIG. 16 is an isometric exploded view of the offset reamer of FIG. 12 from a second viewpoint.

Referring to FIGS. 15-16, the reamer coupler 2204 includes a central longitudinal rotational axis 2205, a head 2288, a drive feature 2292 under the head, and a shaft 2294 between the head 2288 and the drive feature 2292. The reamer coupler 2204 may be referred to as a coupling which connects the offset reamer 2200 to a prime mover or torque source such as a power driver or T-handle so that the reamer head 2202 may be rotated or spun about the axis 2203. The head 2288 may include a drive portion 2296, which may be a hex socket, as illustrated in FIG. 15, a hexalobular socket, or another configuration for torque transmission in at least one rotational direction. The drive feature 2292 may be a threaded shaft, as illustrated in FIG. 16, or another configuration for cooperation with the drive portion 2289 of the socket 2286 of the reamer head 2202 for torque transmission in at least one rotational direction.

The first bushing 2212 includes a tubular body, or tube 2211. A flange 2213 projects circumferentially outwardly around one end of the tube 2211.

The second bushing 2214 includes a tubular body, or tube 2215. A flange 2217 projects circumferentially outwardly around one end of the tube 2215.

The working tip 2206 may be coupled to one end of the shaft 2208 and the handle 2210 may be coupled to the other end of the shaft 2208 to form a handle assembly. The working tip 2206, the shaft 2208, and the handle 2210 may be permanently or temporarily coupled together. For example, the working tip 2206 and/or handle 2210 may be permanently welded to the shaft 2208. Alternatively, the working tip 2206 and/or handle 2210 may be temporarily threaded or snapped to the shaft 2208. The working tip 2206 includes a shaft portion 2272 for connection to the shaft 2208 and a plate portion 2274 that extends obliquely from the shaft portion. The shaft 2208 includes a central longitudinal axis 2209 with which the shaft portion 2272 aligns when the shaft 2208 and the shaft portion 2272 are connected. The plate portion 2274 includes an obverse side 2273, or bone facing side, and a reverse side 2275 opposite the bone-facing side. The plate portion 2274 is pierced by an aperture 2276 or hole which may extend through the obverse side 2273 and the reverse side 2275.

The reamer head 2202, the first bushing 2212, the working tip 2206, the second bushing 2214, and the reamer coupler 2204 are operatively assembled by inserting the tube 2211 of the first bushing 2212 into the aperture 2276 of the working tip 2206 so that the flange 2213 rests against the reverse side 2275; inserting the tube 2215 of the second bushing 2214 into the aperture 2276 of the working tip 2206 so that the flange 2217 rests against the obverse side 2273; inserting the reamer coupler 2204 into the tubes 2211, 2215 so that the head 2288 rests against the flange 2213 and the drive feature 2292 extends beyond the flange 2217; and coupling the drive feature 2292 to the drive portion 2289 of the central socket 2286 of the reamer head, for example by threading the drive feature 2292 into the drive portion 2289. The working tip 2206 may be said to carry the reamer coupler 2204 and the reamer head 2202, as well as the first bushing 2212 and the second bushing 2214. The reamer head 2202, the first bushing 2212, the working tip 2206, the second bushing 2214, and/or the reamer coupler 2204 may include a retention element, such as a ball detent, clip, retaining ring, groove, taper, twist, or the like, to keep the reamer head 2202, the first bushing 2212, the working tip 2206, the second bushing 2214, and/or the reamer coupler 2204 coupled together until intentionally disassembled. The operative assembly of the reamer head 2202, the first bushing 2212, the working tip 2206, the second bushing 2214, and the reamer coupler 2204 may be referred to as a working portion of the offset reamer 2200.

When the reamer head 2202, the first bushing 2212, the working tip 2206, the second bushing 2214, and the reamer coupler 2204 are operatively assembled, at least the reamer head 2202 and the reamer coupler 2204 may be rotationally coupled or fixed together with axes 2203, 2205 collinear. Together, the reamer head 2202 and the reamer coupler 2204 may rotate freely relative to the working tip 2206 about axis 2203; the bushings 2212, 2214 may also rotate freely relative to the reamer coupler 2204 and/or the working tip 2206, or they may be rotationally coupled or fixed to the reamer coupler 2204 or the working tip 2206. The handle assembly of the working tip 2206, the shaft 2208, and the handle 2210 may be manipulated by a user to control the location and orientation of the reamer axis 2203.

The reamer driver 2216, shown in FIGS. 12-17, may be used interchangeably with offset reamers 2100, 2200. The reamer driver 2216 includes a Hudson connector 2218 or torque bit, a shaft 2219, a drive tip 2220 opposite the torque bit, and a central longitudinal rotational axis 2221. The Hudson connector 2218 of the reamer driver 2216 may couple to a prime mover or torque source, such as a power driver or a T-handle. The drive tip 2220 may be directly engaged with the reamer coupler 2204, and rotated by the prime mover about the axis 2221 to turn the reamer coupler 2204 and the reamer head 2202 about axis 2203. In other words, the reamer driver 2216 may be rotationally coupled to the reamer coupler 2204 and the reamer head 2202. For example, the reamer driver 2216 may have a straight hex key drive tip to engage the hex socket drive portion 2296 so that axis 2221 is in line with, or coaxial with, the axis 2203. The reamer driver 2216 may alternatively have a ball drive tip 2220 as shown, which permits the rotational axis 2221 of the reamer driver 2216 to be polyaxially obliquely angled, or polyaxially angularly offset, relative to the rotational axis 2203 of the reamer head 2202. FIG. 17 illustrates an example in which the axis 2221 is obliquely angled, or angularly offset, relative to the axis 2203. In this example with the ball drive tip, the driver axis 2221 may be described as being angularly offset from, or noncollinear with, the rotational axis 2203 of the reamer head 2202, so that the driver axis 2221 and the axis 2203 have no more than a single mathematical point in common, and that only if the driver axis 2221 and the axis 2203 intersect. Therefore, the reamer driver 2216 may be referred to as an offset driver or an offset drive shaft due to the unconstrained angular offset between the axis 2221 and the axis 2203. The reamer driver 2216 may alternatively include other adaptations to permit the reamer driver 2216 to be obliquely angled, or angularly offset, relative to the rotational axis 2203 of the reamer head 2202, such as a universal joint, a flexible shaft portion, a bevel gear acting against the reamer head 2202 and/or the reamer coupler 2204, a ball Torx drive (hexalobular), a ball star drive, or the like. Various ball drive tips may be substituted for the ball hex drive tip 2220 shown, such as Torx, hexalobular, star, or various other polygonal or polylobular shapes. More specifically, the reamer driver 2216 may have a ball drive tip 2220 with five or more corners or points, which may provide a smooth feel with less turbulence or kicking during actuation. While the ball hex key drive tip is an example which provides polyaxial angular offset, other examples may provide a fixed angular offset. In use, the reamer driver 2216 may be angularly repositioned relative to the axis 2203 at any time the user desires, whether or not the driver is being actuated or rotated. The driver 2216 may be repositioned independently of any manipulation of the reamer head axis 2203 or the handle assembly, so that the angular offset between the axis 2203 and the driver axis 2221 is continuously variable.

With continued reference to FIG. 17, axis 2203 and axis 2221 may intersect at a point 2207. As explained above, in some instances axis 2203 and axis 2221 do intersect at a single mathematical point. In other examples, axis 2203 and axis 2221 may be skew, in which case point 2207 may be referred to as a virtual intersection point, or a point where axis 2203 and axis 2221 are closest together. In any case, axis 2221 may move relative to axis 2203 due to manipulation of the reamer driver 2216 while the point 2207 remains at a fixed distance or depth relative to the reamer head 2202 (particularly a fixed distance from the cutting side, measured along axis 2203) or the reamer coupler 2204 (particularly a fixed distance within the drive portion 2296, when the drive portion 2296 is a socket as shown).

Offset reamers 2100, 2200 are mechanically simple designs. The reamer heads 2102, 2202 are captured at the end of angled shafts 2108, 2208 respectively. The shafts are used to position and stabilize the reamer heads 2102, 2202. The reamer heads 2102, 2202 are driven, or turned, by a separate driver, such as reamer driver 2216, which directly engages drive portions 2196, 2296 on the reamer couplers 2104, 2204 respectively. The reamer driver 2216 is shown with a ball hex feature on the distal end that allows the shaft 2219 to be misaligned, angularly offset, or obliquely oriented, relative to the reamer head axis 2203. The specific example shown provides up to 30 degrees of angular misalignment, although any amount of misalignment is contemplated as a matter of design choice. In other words, the magnitude of the angular offset or oblique angle may be greater than zero degrees and less than 180 degrees. The offset reamers 2100, 2200 may be driven by a prime mover or torque source such as a power instrument, or manually using a T-handle. The prime mover may couple directly to a fitting such as a Hudson connector or torque bit of the driver.

The reamer coupler 2104 includes a shaft 2194 which may be a drill tip, and which may protrude through the obverse of the reamer head 2102; and the reamer head 2202 includes a central drill point 2287; both features may eliminate a separate step to drill a pilot hole. The drill tips may be face cutting only, lacking any cutting edges along their long axis. This feature may prevent the drill tips from skiving laterally under load.

Offset reamers 2100, 2200 provide easy clearance around interfering structures, due to the angled shafts 2108, 2208 and handles 2110, 2210 relative to the reamer heads 2102, 2202. The operation of offset reamers 2100, 2200 is stable because the stabilizing action of the handles 2110, 2210 and the torque drive loads are structurally separated. Offset reamers 2100, 2200 may provide effective cutting action due to the direct loading of the cutting head through a separate drive shaft, such as shaft 2219. The drive shaft 2219 need only be angled sufficiently to avoid contact with the interfering structures. The construction of the offset reamers 2100, 2200 is simple and cost effective to manufacture.

A method of using the offset reamer 2100 to prepare an implantation site for the glenoid components will now be described. The method may include the steps of providing the offset reamer 2100, with the handle 2110, the shaft 2108, and a working portion including the working tip 2106, the reamer head 2102, and the reamer coupler 2104; inserting the working portion into a shoulder joint (FIG. 3) along a first trajectory so that the shaft 2194 is in the pilot hole 10; providing the reamer driver 2216, with the shaft 2219, the Hudson connector 2218 or torque bit at one end of the shaft 2219, and the drive tip 2220 at an opposite end of the shaft 2219 from the Hudson connector 2218 or torque bit; coupling the Hudson connector 2218 or torque bit to a prime mover; engaging the drive tip 2220 of the reamer driver 2216 with the drive portion 2196 of the reamer coupler 2104 along a second trajectory which is angularly offset from the first trajectory; actuating the prime mover to rotate the reamer driver 2216 about the axis 2221 to turn the reamer coupler 2204 and the reamer head 2202 about the axis 2203, thereby preparing a reamed surface 14 in the glenoid fossa 4 (FIG. 6); and removing the working portion and the reamer driver 2216.

The step of providing the offset reamer 2100 may include the steps of coupling the handle 2110, shaft 2108, and working tip 2106 together to form a handle assembly; and assembling the reamer head 2102, reamer coupler 2104, and working tip 2106 to form a working portion, wherein the reamer head 2102 and the reamer coupler 2104 are rotationally coupled or fixed together and free to rotate relative to the working tip 2106 about axis 2103.

The step of inserting the working portion into a shoulder joint may include manipulating the handle 2110 to orient or re-orient the working portion. The first trajectory may be between the humeral head and the glenoid fossa 4 (FIG. 3), and aligned with or parallel to the glenoid articular surface. One can appreciate that in the shoulder joint, the first trajectory may be from an anterior or an anterolateral approach to the joint so that the working portion presents its thinnest profile as it enters the joint. The second trajectory may be tangent to the humeral head and aimed at the drive portion 2196 of the reamer coupler 2104. The second trajectory may be from an anterolateral or lateralized approach to the joint so that the drive tip 2220 presents its smallest profile as it enters the joint. Because the working portion and the reamer driver 2216 are separate items, introduced into the joint separately or one at a time, and engaged together in the joint, each item may be introduced into the joint along a trajectory that offers the least resistance to insertion or the least amount of joint distraction or dissection. An integral or non-separable design, by contrast, may have a larger insertion profile which may dictate an insertion trajectory which results in relatively more resistance, joint distraction, and/or dissection.

The step of actuating the prime mover may be preceded by, or performed simultaneously with, a step of reorienting the reamer driver 2216 to lie along a third trajectory which is angularly offset from the first trajectory and the second trajectory. Reorienting the reamer driver 2216 may involve polyaxial rotation of the reamer driver 2216 about the drive tip 2220. The third trajectory may thus be non-coplanar with the first trajectory and the second trajectory.

The preceding method applies equally to the offset reamer 2200. The step of providing the offset reamer 2200 may include the steps of coupling the handle 2210, shaft 2208, and working tip 2206 together to form a handle assembly; and assembling the reamer head 2202, first bushing 2212, second bushing 2214, reamer coupler 2204, and working tip 2206 to form a working portion, wherein the reamer head 2202 and the reamer coupler 2204 are rotationally coupled or fixed together and free to rotate relative to the working tip 2206 about axis 2203.

Figure 18:
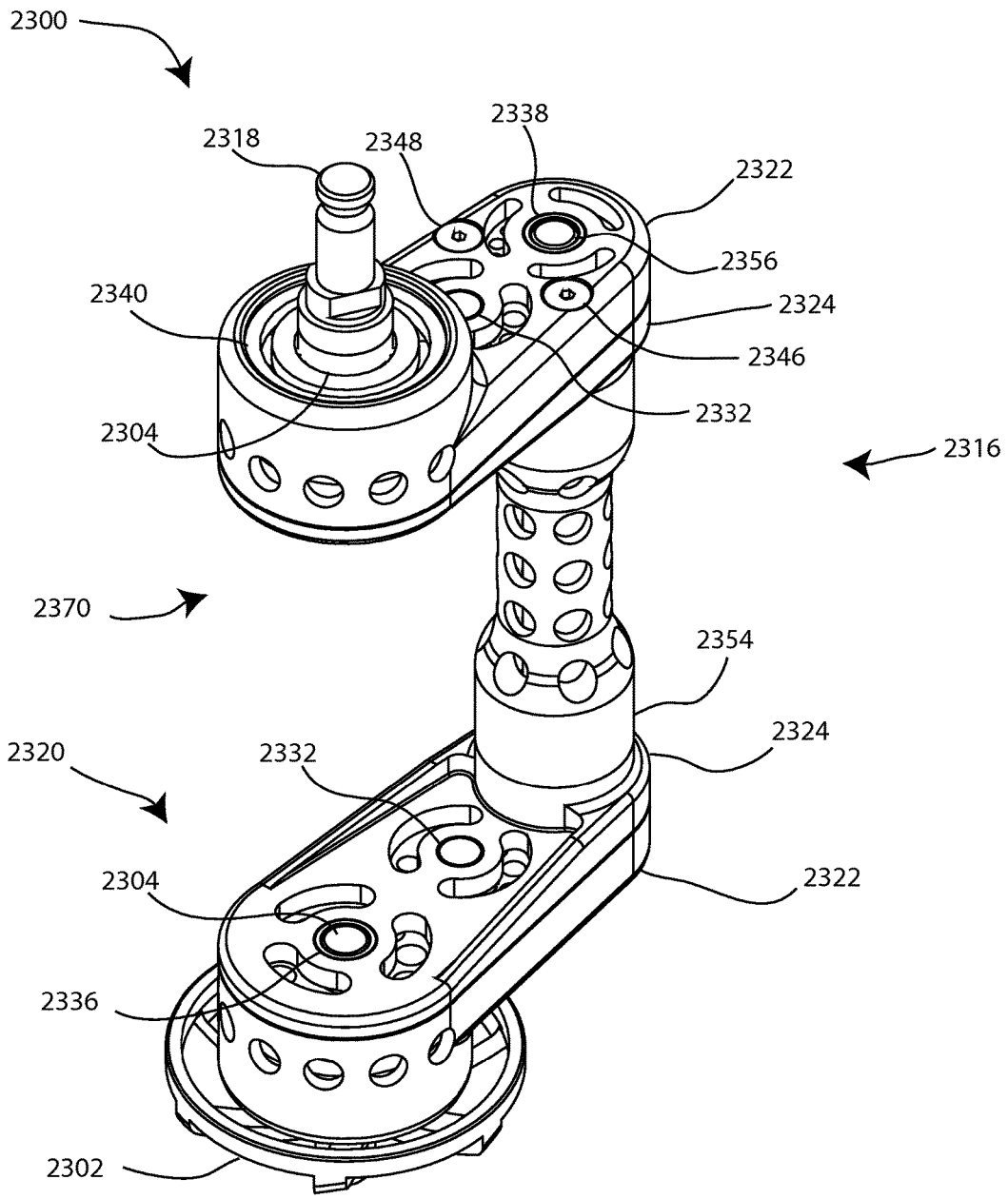
FIG. 18 is an isometric view of yet another offset reamer.
Figure 19:
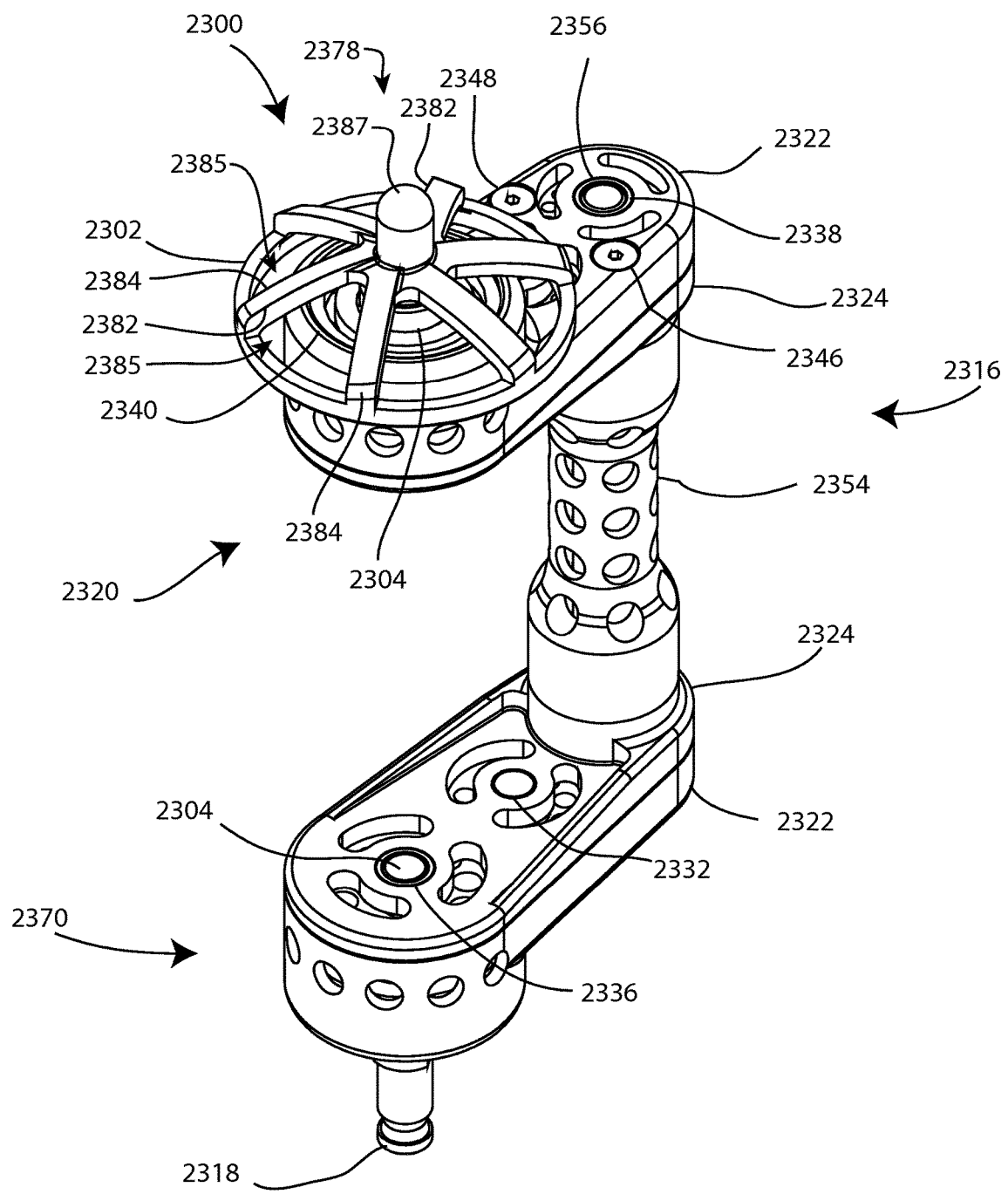
FIG. 19 is an isometric view of the offset reamer of FIG. 18 from a second viewpoint.

Referring to FIG. 18, yet another offset reamer 2300 includes a reamer head 2302, an offset assembly 2316, and a Hudson connector 2318 or torque bit which receives torque from a prime mover. FIGS. 18-24 show various views of offset reamer 2300.

Figure 20:
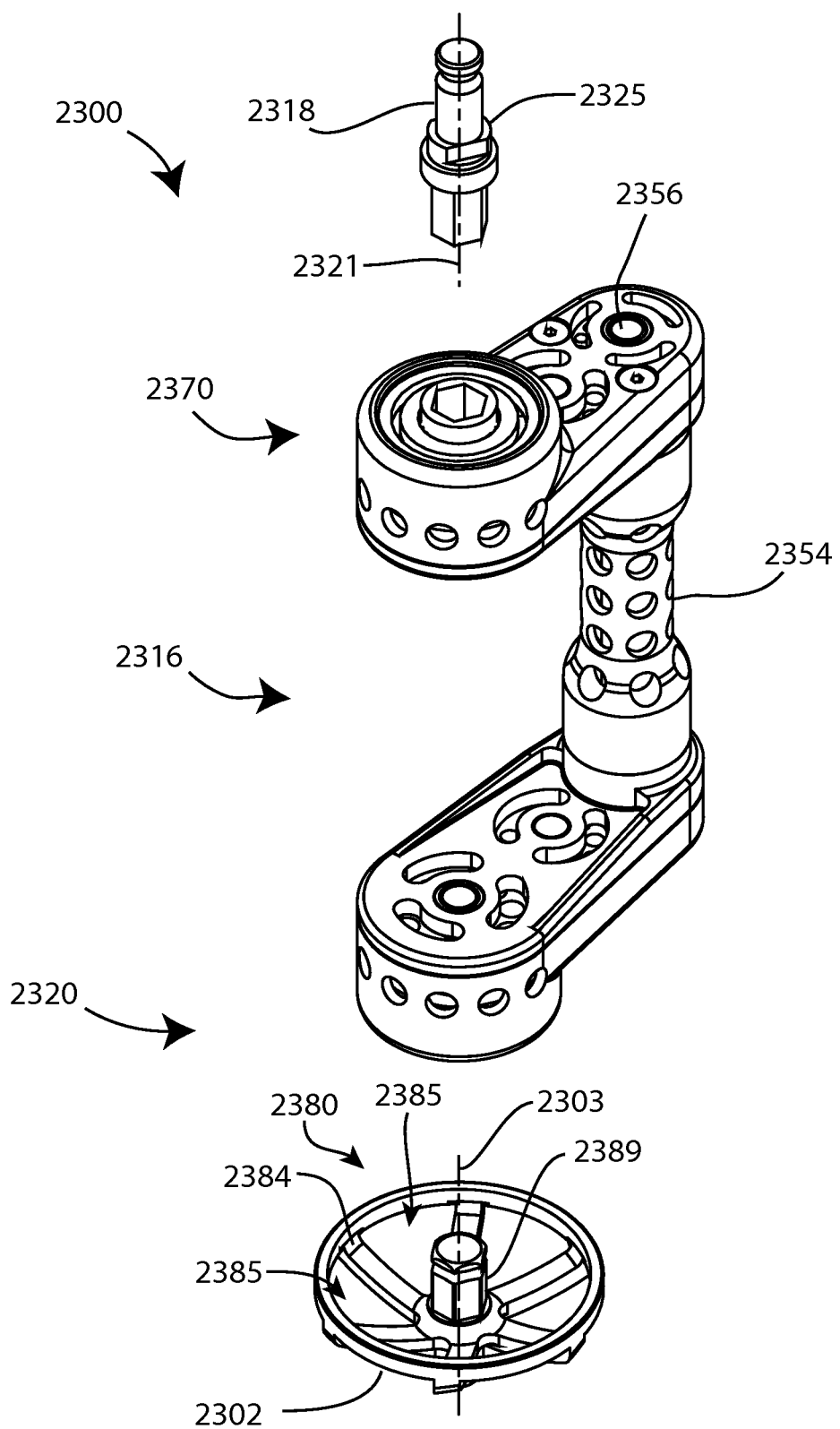
FIG. 20 is an isometric exploded view of the offset reamer of FIG. 18.

The reamer head 2302 is a round part with a central longitudinal rotational axis 2303, a convex obverse side 2378, or bone-facing side or cutting side (FIG. 19), and a reverse side 2380 (FIG. 20). The obverse side 2378 may be flat or concave in other examples devoted to other joints around the body. The obverse side 2378 includes bone removal features 2382, which may be teeth, serrations, ridges and grooves, knurling, a sandpaper texture, or the like. In the example shown, the bone removal features 2382 are sharpened edges on radial arms 2384 of the reamer head 2302. Six arms 2384 are shown in the example, although any number of arms may be provided. The arms 2384 in the example are separated by windows 2385 or apertures. In other examples, the reamer head 2302 may share some or all of the characteristics of reamer heads 2102, 2202 or body 1308 disclosed above. The reamer head 2302 includes a central drive portion 2389 protruding from the reverse side 2380. The drive portion 2389 may be a hex key, as illustrated in FIG. 20, or another configuration for torque transmission in at least one rotational direction. The reamer head 2302 is illustrated with a central boss or drill point 2387 protruding from the obverse side 2378. In this example, the central boss or drill point 2387 is integral with the reamer head 2302. This feature may include cutting flutes at least along its leading tip. The central boss or drill point 2387 may be spring loaded, and may be biased to be normally extended or normally retracted.

Figure 22:
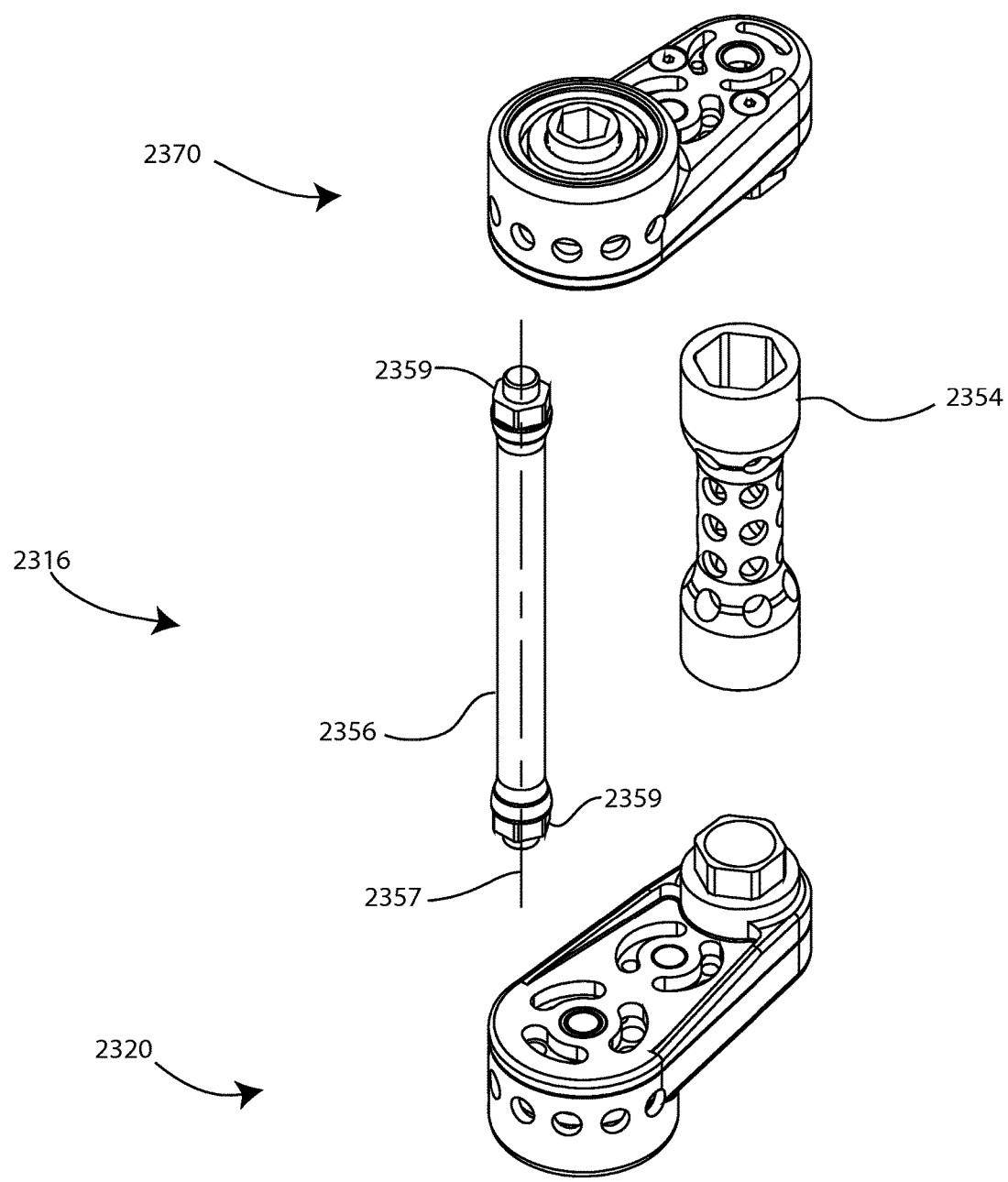
FIG. 22 is an isometric exploded view of an offset assembly of the offset reamer of FIG. 18.

Referring to FIG. 22, the offset assembly 2316 includes a first gear assembly 2320, a sleeve 2354, and an offset drive shaft 2356. The offset assembly 2316 may include a second gear assembly 2370.

Figure 23:
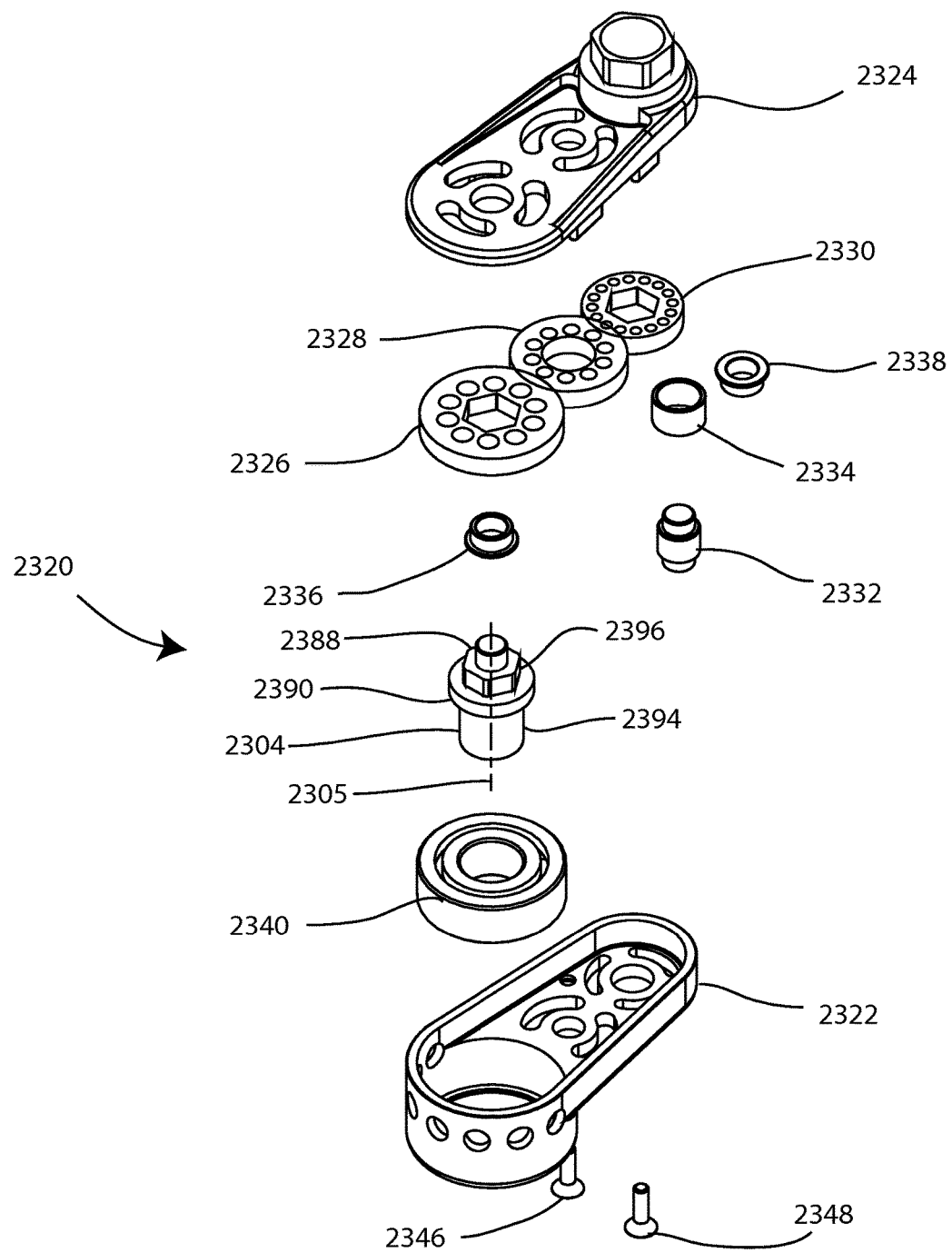
FIG. 23 is an isometric exploded view of a reamer gear assembly of the offset reamer of FIG. 18.
Figure 24:
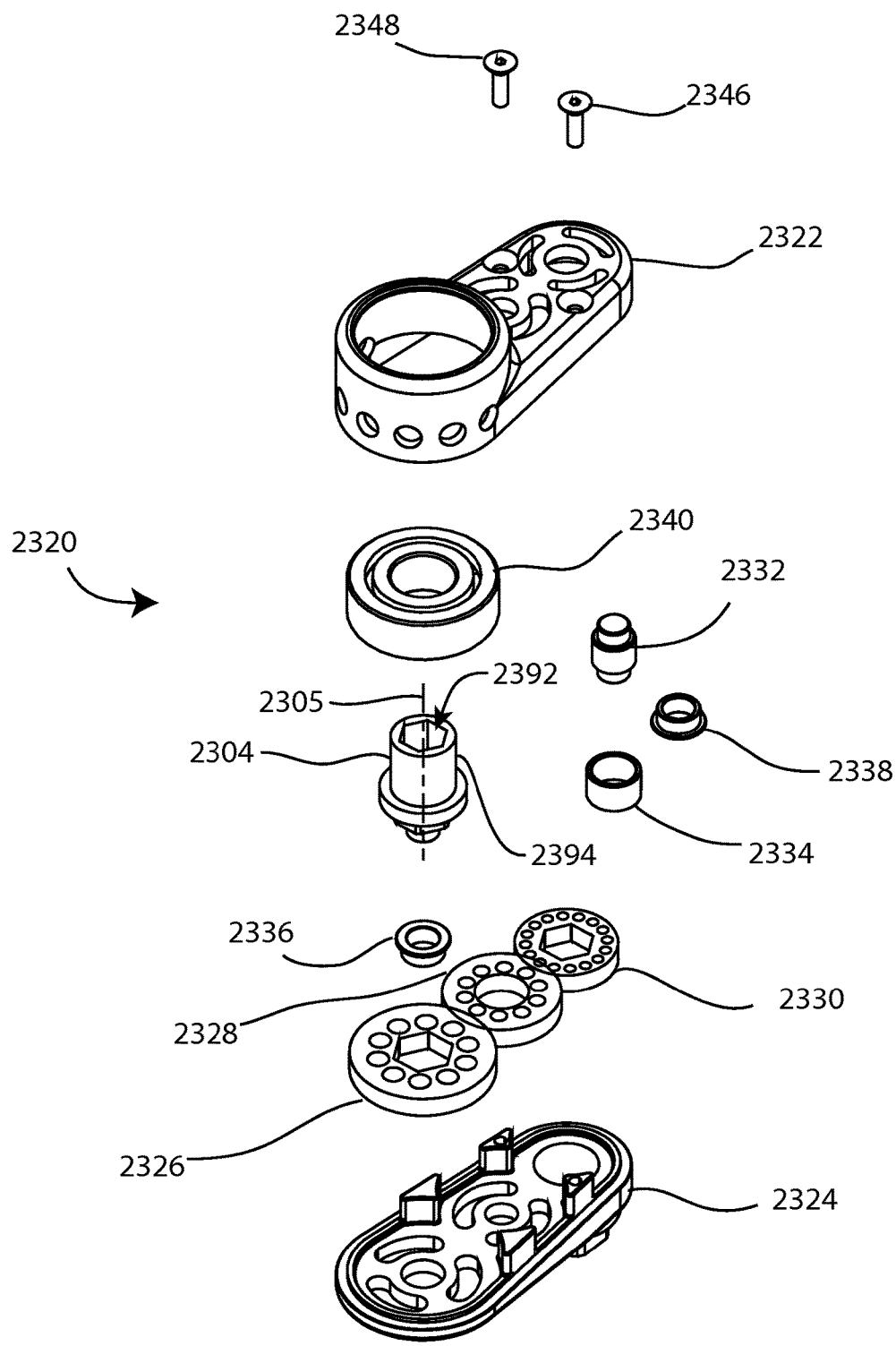
FIG. 24 is an isometric exploded view of the reamer gear assembly of FIG. 23 from a second viewpoint.

Referring to FIGS. 23-24, the first gear assembly 2320 includes a drive shaft 2304, a first housing 2322, a second housing 2324, a first gear 2326, a second gear 2328, a third gear 2330, an idler pin 2332, an idler bushing 2334, a first drive bushing 2336, a second drive bushing 2338, a bearing assembly 2340, a first fastener 2346, and a second fastener 2348.

Referring to FIGS. 23-24, the drive shaft 2304 includes a central longitudinal rotational axis 2305, a head 2388, a flange 2390 under the head, a drive feature 2392 under the flange, and a shaft 2394 under the flange. The drive shaft 2304 may be referred to as a coupling which connects the offset reamer 2300 to a prime mover or torque source such as a power driver or T-handle so that the reamer head 2302 may be rotated or spun about the axis 2303. The head 2388 may include a drive portion 2396, which may be a hex key, as illustrated in FIG. 23, or another configuration for torque transmission in at least one rotational direction. The drive feature 2392 may be a hex socket, as illustrated in FIG. 24, or another configuration for cooperation with the drive portion 2389 of the reamer head 2302, or for cooperation with a prime mover or the Hudson connector 2318 or torque bit, for torque transmission in at least one rotational direction.

The gears 2326, 2328, 2330, idler pin 2332, and bushings 2334, 2336, 2338 serve to transfer torque laterally between the drive shafts 2304 and the offset drive shaft 2356, and may preserve the clockwise or counterclockwise rotational direction of the torque. Bevel gears, universal joints, flexible shafts, or other torque offset couplings, torque offset apparatus, torque transfer apparatus, or gearboxes may be substituted for the gears 2326, 2328, 2330, idler pin 2332, and bushings 2334, 2336, 2338. The gears or equivalents may be said to indirectly couple the drive shaft 2304 to the offset drive shaft 2356. While the offset drive shaft 2356 is shown parallel to and laterally offset from the drive shafts 2304 by a non-zero distance, other angular relationships of these parts are contemplated.

The first housing 2322, the second housing 2324, the first fastener 2346, and the second fastener 2348 serve to enclose and stabilize the drive shaft 2304, the gears 2326, 2328, 2330, the idler pin 2332, the bushings 2334, 2336, 2338, and the bearing assembly 2340.

When the first gear assembly 2320 is operatively assembled, the drive shaft 2304 is rotationally coupled to the first gear 2326. The second gear 2328 meshes with the first gear 2326 and the third gear 2330 for torque transmission.

The second gear assembly 2370 may be identical to the first gear assembly 2320.

The offset drive shaft 2356 includes a central longitudinal rotational axis 2357 and drive feature 2359 at one end of the offset drive shaft. A second drive feature 2359 may be included. The drive feature 2359 may be a hex key as illustrated in FIG. 22, or another configuration for torque transmission in at least one rotational direction. The drive feature 2359 may directly receive torque from a prime mover if the second gear assembly 2370 is not present.

Figure 21:
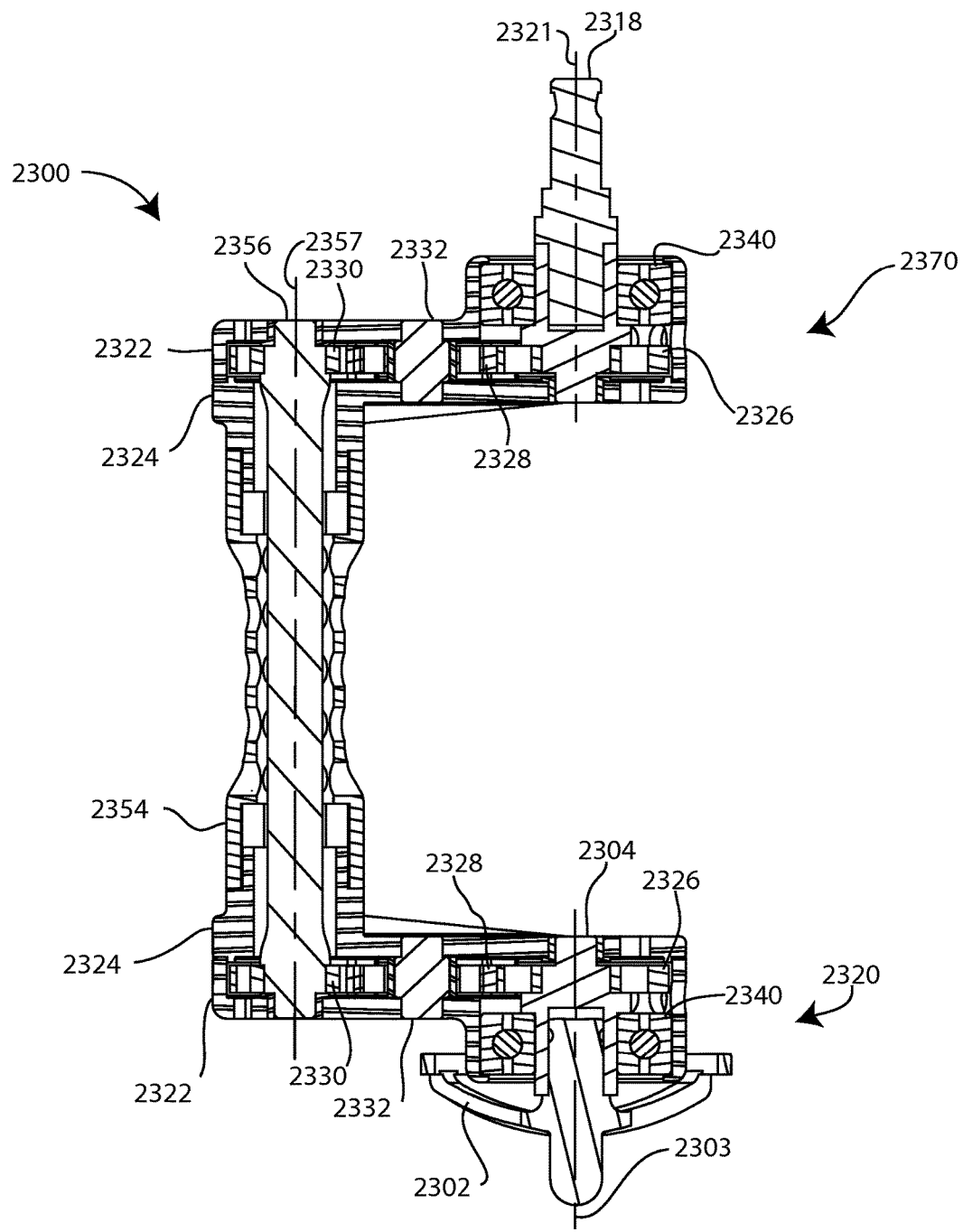
FIG. 21 is a cross sectional view through the offset reamer of FIG. 18.

When the offset assembly 2316 is operatively assembled, the offset drive shaft 2356 is rotationally coupled to the third gear 2330 of the first gear assembly 2320, and to the third gear 2330' of the second gear assembly 2370, if present. The axis 2303 and the axis 2356 may be described as parallel with a distance offset having a magnitude greater than zero, so that the axis 2303 and the axis 2356 have zero mathematical points in common. The same applies to axis 2321 and axis 2356. Axis 2303 and axis 2321 may be collinear, as shown in FIG. 21, or parallel, or another orientation.

The Hudson connector 2318 or torque bit receives torque from a prime mover. The Hudson connector 2318 includes a central longitudinal rotational axis 2321, a drive portion 2323, and a drive feature 2325.

When the offset reamer 2300 is operatively assembled, the reamer head 2302 is rotationally coupled or fixed to the drive shaft 2304 of the first gear assembly 2320 with axes 2303, 2305 collinear, and the Hudson connector 2318 or torque bit is rotationally coupled or fixed to the drive shaft 2304' of the second gear assembly 2370, if present, with axes 2321, 2305' collinear.

Offset reamer 2300 uses two gear assemblies 2320, 2370 to establish an offset drive shaft that reaches around interfering structures to deliver torque from a driver to the reamer head 2302. The two gear assemblies 2320, 2370 are identical. On one side 2320, the reamer head 2302 is coupled to the drive shaft 2304 and both components rotate together about axis 2303; therefore, the drive shaft 2304 may be referred to as a reamer coupler 2304. On the opposite side 2370, a Hudson connector 2318 couples directly to another drive shaft 2304' and thence to a prime mover or torque source, which drives the Hudson connector 2318 and the drive shaft 2304' to rotate about axis 2321. The sleeve 2354 of the offset reamer 2300 may be used as an offset handle. The offset reamer 2300 may be operated using a familiar prime mover or torque source, such as a power driver or T-handle, coupled directly to the Hudson connector and indirectly to the offset drive shaft 2356 by way of the gears. A single size offset reamer 2300 may be used with all reamer sizes. Multiple driver interfaces may be used instead of the one shown, allowing the offset reamer 2300 to be used with many instrument brands or styles.

The design of offset reamer 2300 features ease of use equivalent to a conventional straight reamer while eliminating shaft contact with interfering structures. The prime mover or torque source axis of rotation is co-axial with the reamer head axis of revolution. This provides a good visual reference to ensure that the reamer is oriented properly relative to the bone surface. Additionally, this feature allows all axial force to be transferred to the reamer along its natural axis.

Figure 25:
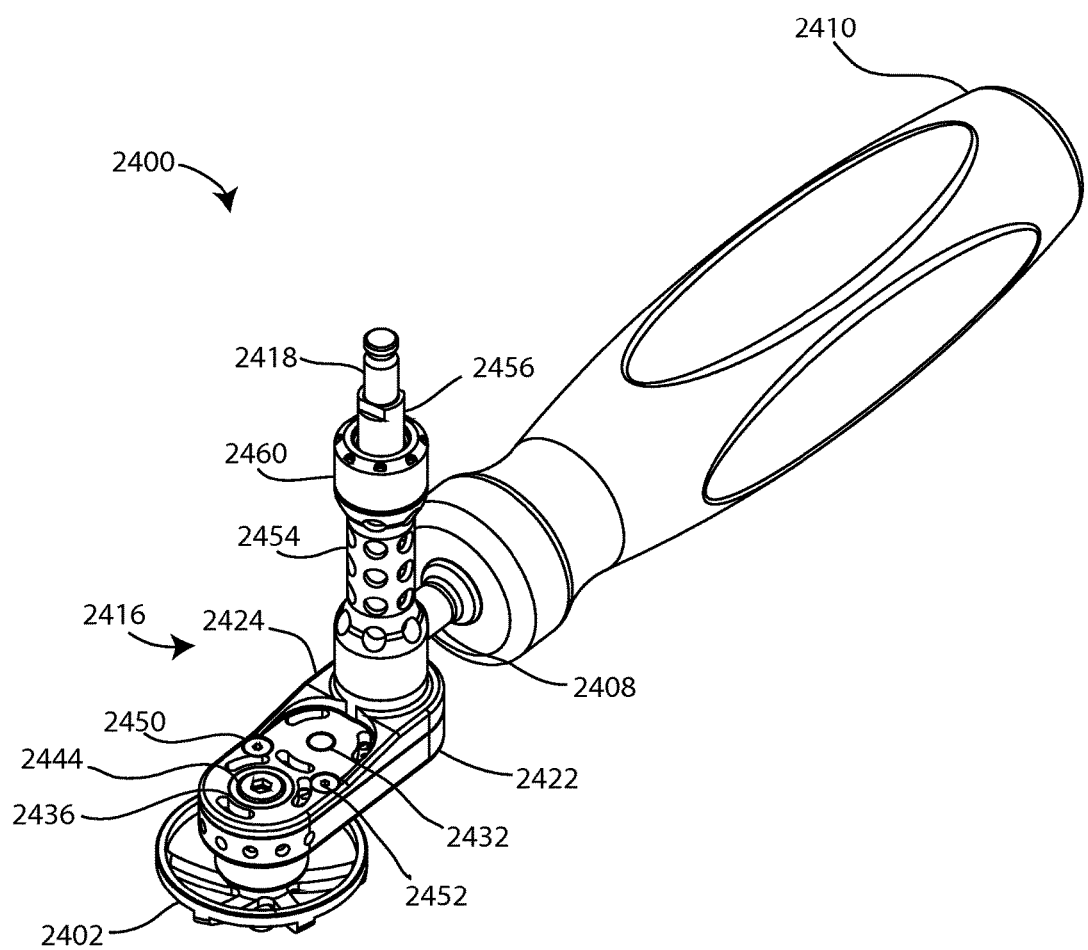
FIG. 25 is an isometric view of yet another offset reamer.
Figure 26:
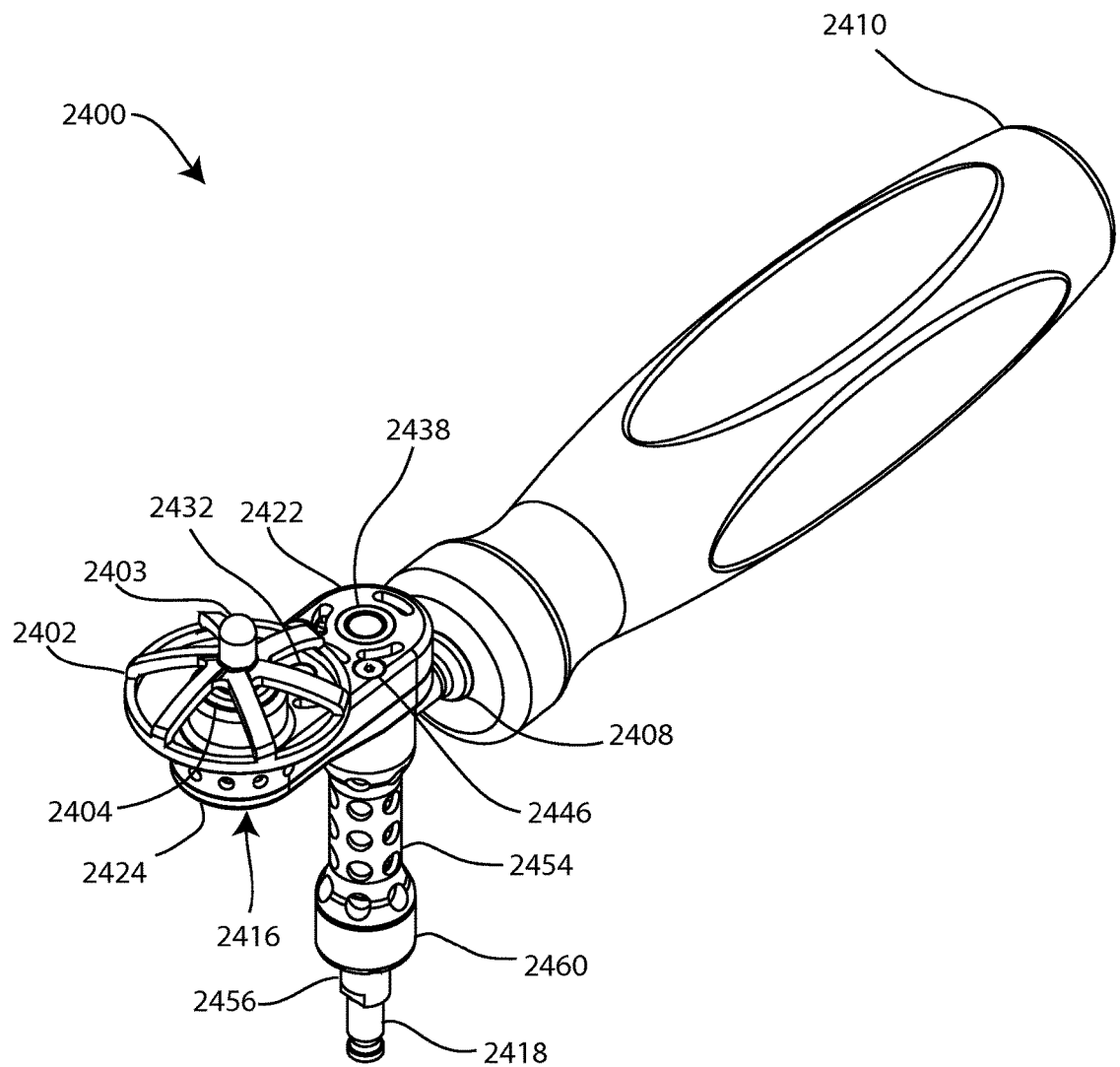
FIG. 26 is an isometric view of the offset reamer of FIG. 25 from a second viewpoint.

Referring to FIG. 25, yet another offset reamer 2400 includes a reamer head 2402, an offset assembly 2416, a shaft 2408, and a handle 2410. FIGS. 25-31 show various views of offset reamer 2400.

Figure 30:
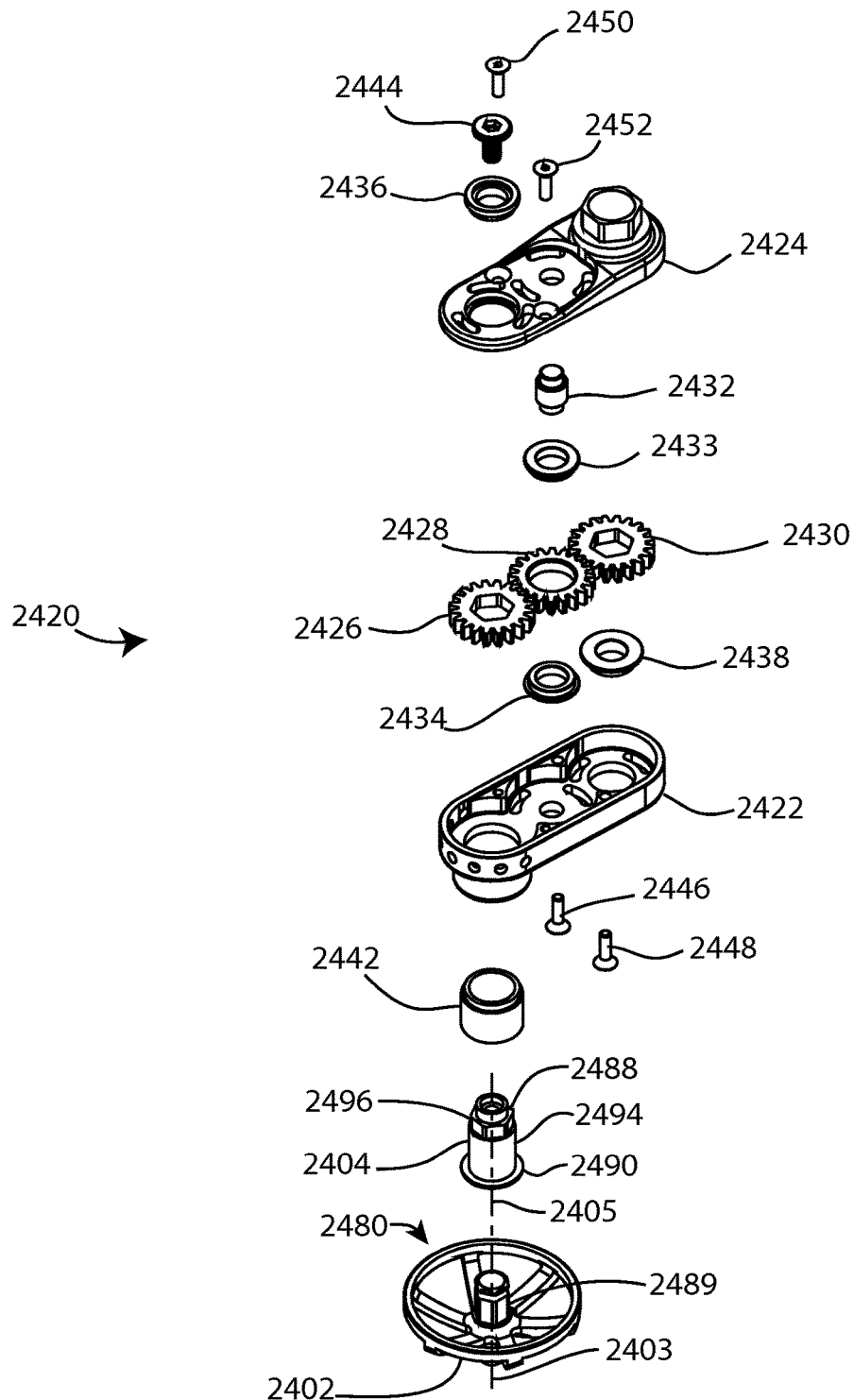
FIG. 30 is an isometric exploded view of a reamer gear assembly of the offset reamer of FIG. 25.

The reamer head 2402 is a round part with a central longitudinal rotational axis 2403, a convex obverse side 2478, or bone-facing side or cutting side (FIG. 31), and a reverse side 2480 (FIG. 30). The obverse side 2478 may be flat or concave in other examples devoted to other joints around the body. The obverse side 2478 includes bone removal features 2482, which may be teeth, serrations, ridges and grooves, knurling, a sandpaper texture, or the like. In the example shown, the bone removal features 2482 are sharpened edges on radial arms 2484 of the reamer head 2402. Six arms 2484 are shown in the example, although any number of arms may be provided. The arms 2484 in the example are separated by windows 2485 or apertures. In other examples, the reamer head 2402 may share some or all of the characteristics of reamer heads 2102, 2202 or body 1308 disclosed above. The reamer head 2402 includes a central drive portion 2489 protruding from the reverse side 2480. The drive portion 2489 may be a hex key, as illustrated in FIG. 30, or another configuration for torque transmission in at least one rotational direction. The reamer head 2402 is illustrated with a central boss or drill point 2487 protruding from the obverse side 2478. In this example, the central boss or drill point 2487 is integral with the reamer head 2402. This feature may include cutting flutes at least along its leading tip. The central boss or drill point 2487 may be spring loaded, and may be biased to be normally extended or normally retracted.

Figure 27:
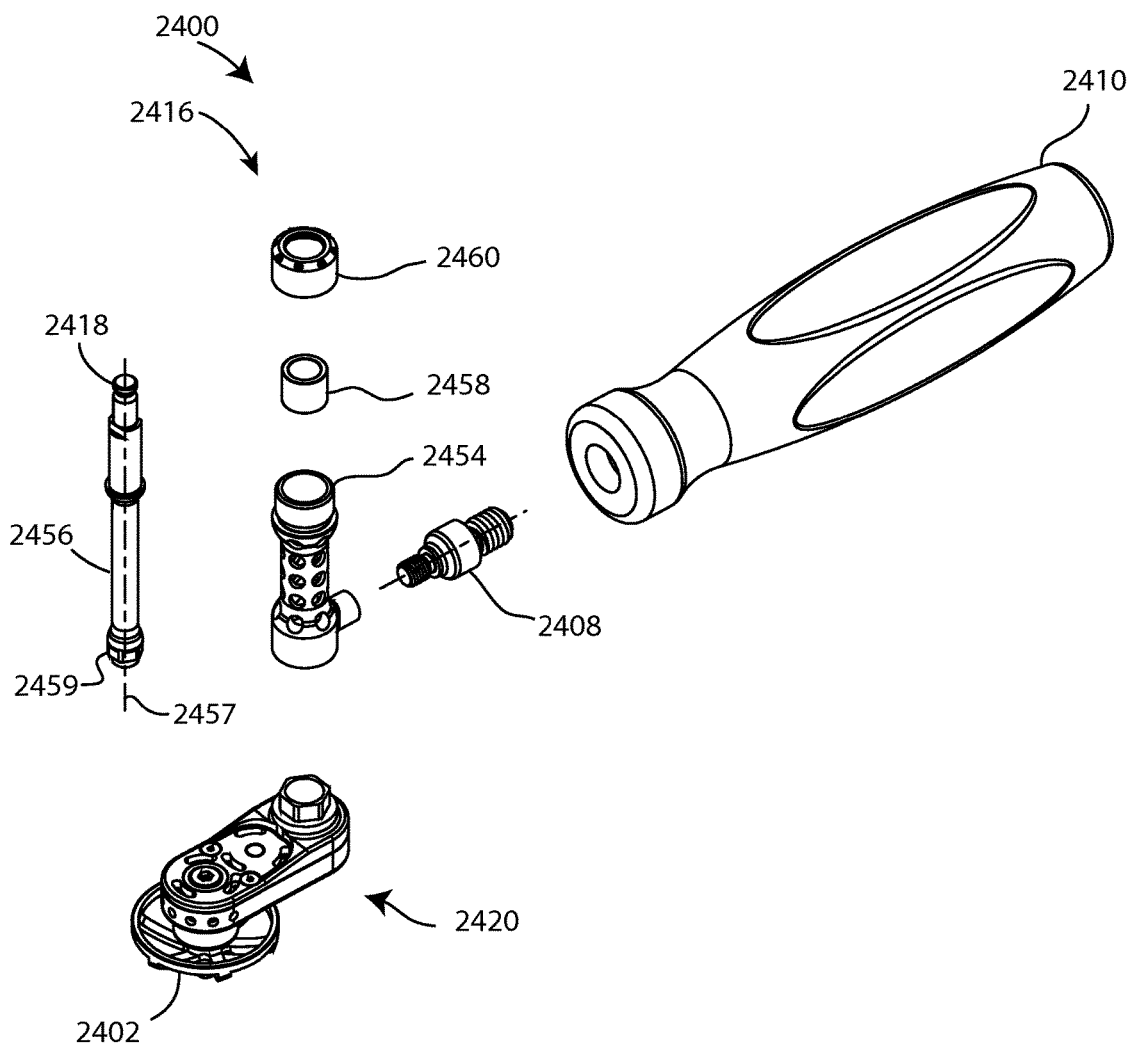
FIG. 27 is an isometric exploded view of the offset reamer of FIG. 25.

Referring to FIG. 27, the offset assembly 2416 includes a gear assembly 2420, a sleeve 2454, an offset drive shaft 2456, a Hudson bushing 2458, and a bushing cap 2460. The offset assembly may include a second gear assembly (not shown) which may be identical to gear assembly 2420, and which may be arranged in the offset reamer 2400 in the manner described above for second gear assembly 2370 of offset reamer 2300.

Figure 31:
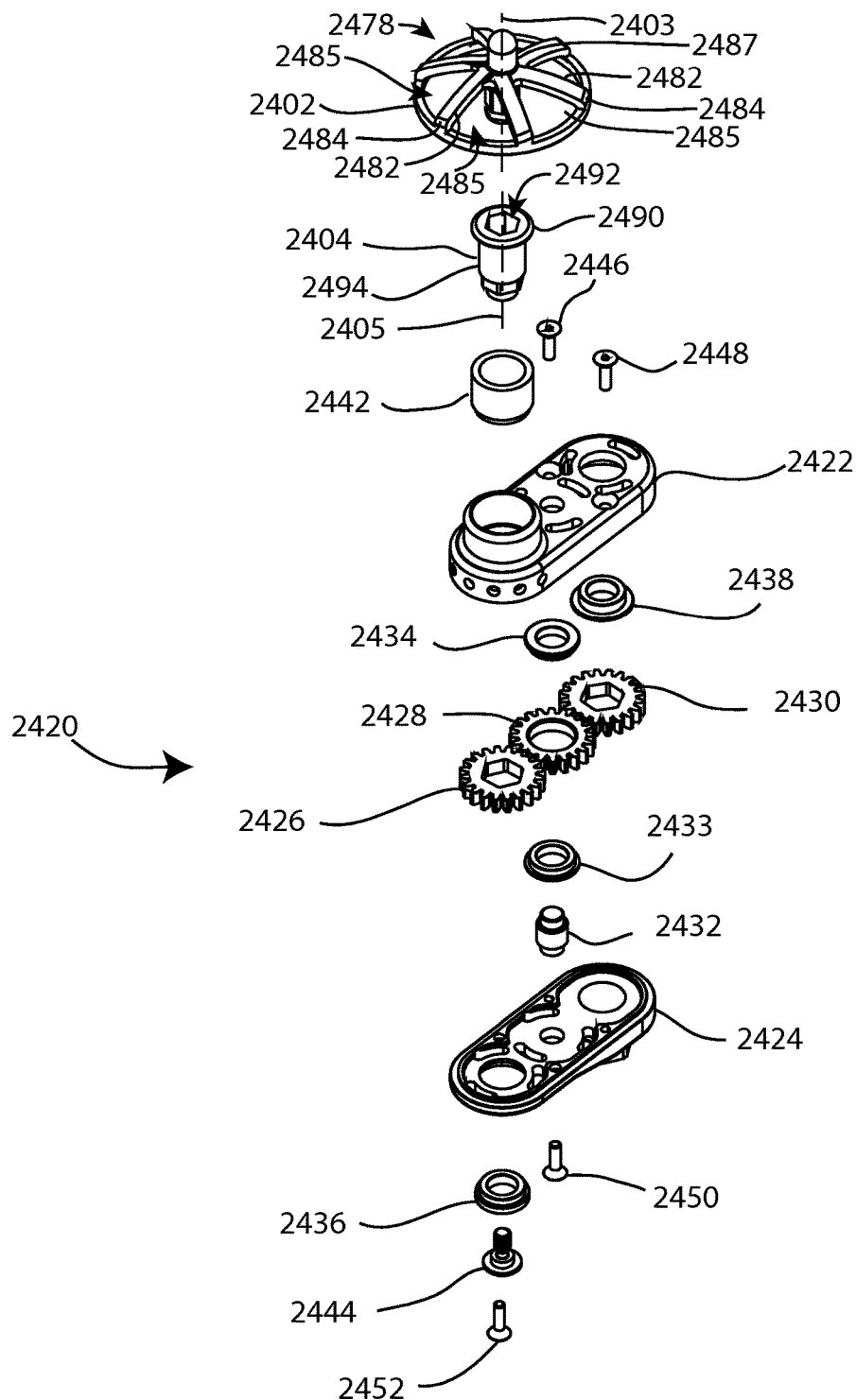
FIG. 31 is an isometric exploded view of the reamer gear assembly of FIG. 30 from a second viewpoint.

Referring to FIGS. 30-31, the gear assembly 2420 includes a drive shaft 2404, a first housing 2422, a second housing 2424, a first gear 2426, a second gear 2428, a third gear 2430, an idler pin 2432, a first idler bushing 2433, a second idler bushing 2434, a first drive bushing 2436, a second drive bushing 2438, a main bushing 2442, a shoulder screw 2444, a first fastener 2446, a second fastener 2448, a third fastener 2450, and a fourth fastener 2452.

The drive shaft 2404 includes a central longitudinal rotational axis 2405, a head 2488, a flange 2490 under the head, a drive feature 2492 opposite the head, and a shaft 2494 under the head. The drive shaft 2404 may be referred to as a coupling which connects the offset reamer 2400 to a prime mover or torque source such as a power driver or T-handle so that the reamer head 2402 may be rotated or spun about the axis 2403. The head 2488 may include a drive portion 2496, which may be a hex key, as illustrated in FIG. 30, or another configuration for torque transmission in at least one rotational direction. The drive feature 2492 may be a hex socket, as illustrated in FIG. 31, or another configuration for cooperation with the drive portion 2489 of the reamer head 2402 for torque transmission in at least one rotational direction.

The gears 2426, 2428, 2430, idler pin 2432, and bushings 2433, 2434, 2436, 2438, 2442 serve to transfer torque laterally between the drive shafts 2404 and the offset drive shaft 2456, and may preserve the clockwise or counterclockwise rotational direction of the torque. Bevel gears, universal joints, flexible shafts, or other torque offset couplings, torque offset apparatus, torque transfer apparatus, or gearboxes may be substituted for the gears 2426, 2428, 2430, idler pin 2432, and bushings 2433, 2434, 2436, 2438, 2442.

The gears or equivalents may be said to indirectly couple the drive shaft 2404 to the offset drive shaft 2456. While the offset drive shaft 2456 is shown parallel to and laterally offset from the drive shaft 2404 by a non-zero distance, other angular relationships of these parts are contemplated.

The first housing 2422, the second housing 2424, the shoulder screw 2444, the first fastener 2446, the second fastener 2448, the third fastener 2450, and the fourth fastener 2452 serve to enclose and stabilize the drive shaft 2404, the gears 2426, 2428, 2430, idler pin 2432, and bushings 2433, 2434, 2436, 2438, 2442.

When the first gear assembly 2420 is operatively assembled, the drive shaft 2404 is rotationally coupled to the first gear 2426. The second gear 2428 meshes with the first gear 2426 and the third gear 2430 for torque transmission.

Figure 28:
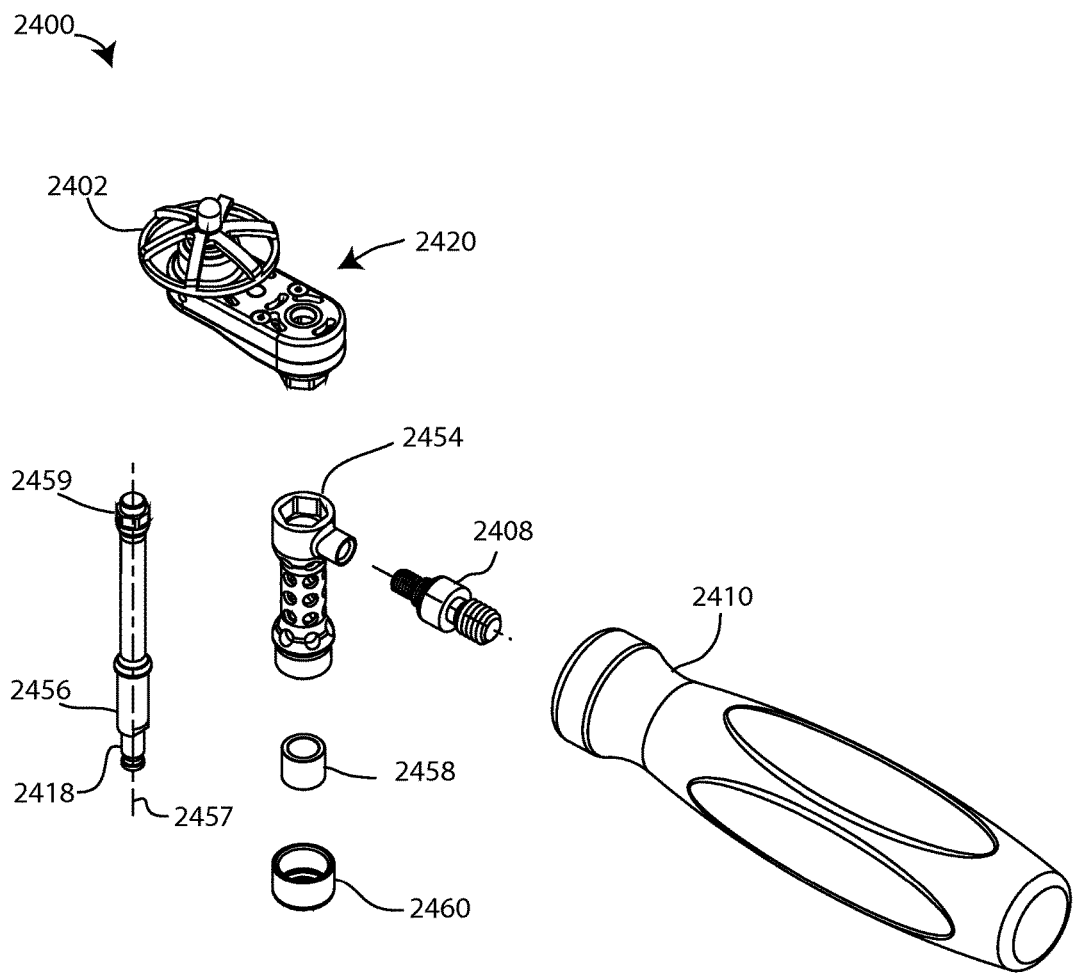
FIG. 28 is an isometric exploded view of the offset reamer of FIG. 25 from a second viewpoint.
Figure 29:
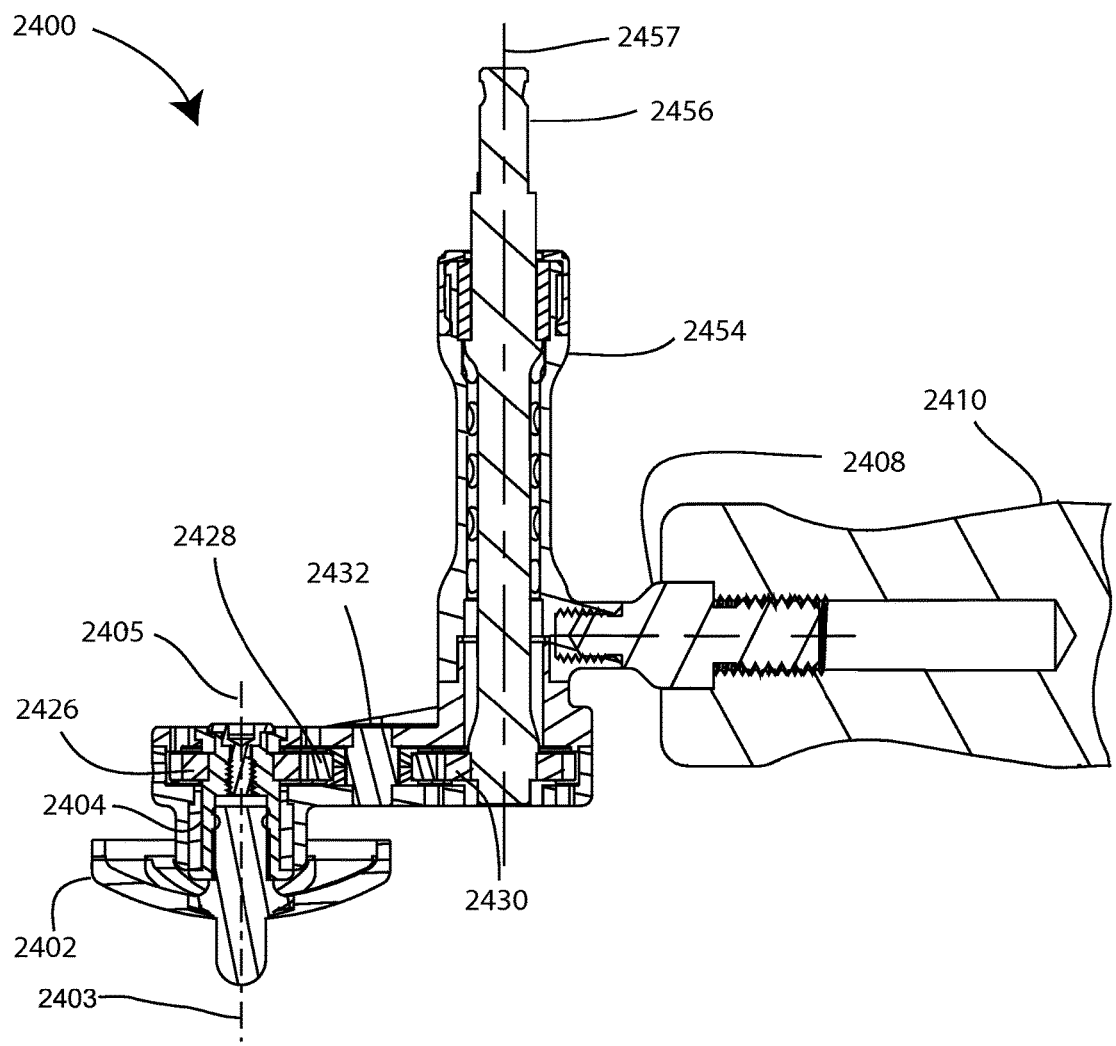
FIG. 29 is a cross sectional view through the offset reamer of FIG. 25, a portion of the handle omitted.

Referring to FIGS. 27-28, the offset drive shaft 2456 includes a central longitudinal rotational axis 2457, a drive feature 2459 at one end of the offset drive shaft, and a Hudson connector 2418 or torque bit at the other end of the offset drive shaft. The drive feature 2459 may be a hex key as illustrated in FIGS. 27-28, or another configuration for torque transmission in at least one rotational direction. The Hudson connector 2418 or torque bit receives torque from a prime mover.

When the offset assembly 2416 is operatively assembled, the offset drive shaft 2456 is rotationally coupled to the third gear 2430 of the first gear assembly 2420, and to the third gear of the second gear assembly, if present. The axis 2405 and the axis 2456 may be described as parallel with a distance offset having a magnitude greater than zero, so that the axis 2405 and the axis 2456 have zero mathematical points in common.

When the offset reamer 2400 is operatively assembled, the reamer head 2402 is rotationally coupled or fixed to the drive shaft 2404 of the first gear assembly 2420 with axes 2403, 2405 collinear.

The offset reamer 2400 is similar to the offset reamer 2300 in that offset reamer 2400 utilizes a gear assembly 2420 to move an offset drive shaft 2456 which is offset from, but parallel to, the reamer head axis of revolution 2403. A handle 2410 has been added in this example to locate and stabilize the offset reamer 2400 during use. The handle 2410 permits the user to exert a counter-moment to compensate for any moment due to the offset shaft arrangement. The handle 2410 may also be included in offset reamer 2300. A drill tip 2487 is included on the reamer head 2402 to combine the steps of creating a pilot hole and reaming the bone surface. A three-gear construct 2426, 2428, 2430, similar to that described for offset reamer 2300, is employed to create the desired lateral offset between axis 2457 and axis 2403. However, in this case, the ball bearing assemblies 2340 have been replaced by bushing style bearings 2442, 2433, 2434, 2436, 2438 used throughout to minimize the overall size and volume of the offset reamer 2400. Other offset constructs may be substituted.

The design of offset reamer 2400 features a simple design that may have an attractive cost of goods. Offset reamer 2400 has a small, compact design. Parallel reamer head and offset shaft axes provide a good visual indicator for reamer orientation. A large handle provides good stability.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Coatings may be present. Different materials may be used within a single part. Any component disclosed herein may be colored, coded or otherwise marked to make it easier for a user to identify the type and size of the component, the setting, the function(s) of the component, and the like.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the examples of the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C.§112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A system comprising:
an arthroplasty implant component comprising an articular surface and an opposite bone-facing surface; and
a reamer system comprising a reamer head, a reamer coupler, and an offset drive shaft, wherein the reamer head is rotationally coupled to the reamer coupler, wherein the reamer coupler is detachably rotationally coupled to the offset drive shaft, wherein the reamer head and the reamer coupler rotate about a first rotational axis, and the offset drive shaft rotates about a second rotational axis, wherein the second rotational axis is obliquely angled relative to the first rotational axis, wherein the second rotational axis intersects the first rotational axis at a point;
wherein the reamer head and the reamer coupler are coupled together to form a working portion, wherein the working portion presents its thinnest profile as the working portion enters a joint between first and second bones along a first trajectory that is aligned with an articular surface of the first bone.

2. The system of claim 1, wherein the second rotational axis is obliquely angled relative to the first rotational axis, with a magnitude that is greater than zero degrees and less than 180 degrees.

3. The system of claim 2, wherein the second rotational axis is obliquely angled relative to the first rotational axis, with a magnitude that is less than or equal to 30 degrees.

4. The system of claim 1, wherein the second rotational axis has a conical range of motion relative to the first rotational axis when the reamer system is operatively assembled and in use to prepare an implantation site for the arthroplasty implant component.

5. The system of claim 1, wherein the reamer system comprises a handle assembly, wherein the handle assembly comprises a working tip, a handle shaft coupled to the working tip, and a handle coupled to the handle shaft opposite the working tip, wherein the working tip carries the reamer head and the reamer coupler, wherein the reamer head and the reamer coupler rotate freely relative to the working tip.

6. The system of claim 5, wherein the reamer system comprises at least one bushing between the working tip and the reamer coupler.

7. The system of claim 1, wherein the reamer head and the reamer coupler are in a fixed concentric relationship relative to the first rotational axis.

8. A system comprising:
an arthroplasty implant component comprising an articular surface and an opposite bone-facing surface; and
a reamer system comprising a reamer head, a reamer coupler, and an offset drive shaft, wherein the reamer head is rotationally coupled to the reamer coupler, wherein the reamer coupler is detachably rotationally coupled to the offset drive shaft, wherein the reamer head and the reamer coupler rotate about a first rotational axis, and the offset drive shaft rotates about a second rotational axis, wherein the first rotational axis and the second rotational axis are noncollinear;
wherein the reamer head and the reamer coupler are coupled together to form a working portion, wherein the working portion has a smaller profile when viewed transverse to the first rotational axis and a larger profile when viewed along the first rotational axis, wherein the working portion presents its thinnest profile as the working portion enters a joint between first and second bones along a first trajectory that is aligned with an articular surface of the first bone.

9. The system of claim 8, wherein the second rotational axis forms an angle with the first rotational axis, wherein the angle is greater than zero degrees and less than 180 degrees.

10. The system of claim 9, wherein the angle is less than or equal to 30 degrees.

11. The system of claim 8, wherein the second rotational axis is free to move polyaxially relative to the first rotational axis when the reamer system is operatively assembled and in use to prepare an implantation site for the arthroplasty implant component.

12. The system of claim 8, wherein the reamer system comprises a handle assembly, wherein the handle assembly comprises a working tip, a handle shaft coupled to the working tip, and a handle coupled to the handle shaft opposite the working tip, wherein the working tip carries the reamer head and the reamer coupler, wherein the reamer head and the reamer coupler rotate freely relative to the working tip.

13. The system of claim 12, wherein the reamer system comprises at least one bushing between the working tip and the reamer coupler.

14. A system comprising:
an arthroplasty implant component comprising an articular surface and an opposite bone-facing surface; and
a reamer system comprising a reamer head, a reamer coupler, an offset drive shaft, and a handle assembly;
wherein the handle assembly comprises a working tip, a handle shaft coupled to the working tip, and a handle coupled to the handle shaft opposite the working tip, wherein the working tip carries the reamer head and the reamer coupler, wherein the reamer head and the reamer coupler rotate freely relative to the working tip;

wherein, when the reamer system is operatively assembled and in use to prepare an implantation site for the arthroplasty implant component, the reamer head is rotationally coupled to the reamer coupler, the reamer coupler is detachably rotationally coupled to the offset drive shaft, the reamer head and the reamer coupler rotate about a first rotational axis, and the offset drive shaft rotates about a second rotational axis, wherein the first rotational axis and the second rotational axis have no more than one point in common;

wherein the reamer head, the reamer coupler, and the working tip are coupled together to form a working portion, wherein the working portion has a smaller profile when viewed transverse to the first rotational axis and a larger profile when viewed along the first rotational axis, wherein the working portion presents its thinnest profile as the working portion enters a joint between first and second bones along a first trajectory that is aligned with an articular surface of the first bone.

15. The system of claim 14, wherein the first rotational axis and the second rotational axis have zero points in common.

16. The system of claim 14, wherein the second rotational axis forms an angle with the first rotational axis, wherein the angle is less than or equal to 30 degrees.

17. The system of claim 14, wherein the first rotational axis and the second rotational axis intersect at a single mathematical point, wherein, when the reamer system is operatively assembled and in use to prepare an implantation site for the arthroplasty implant component, the second rotational axis has a range of motion relative to the first rotational axis in the shape of a cone, wherein the cone comprises an apex that lies on the mathematical point.

* * * * *